(12) United States Patent
Kostic et al.

(10) Patent No.: US 11,723,835 B2
(45) Date of Patent: *Aug. 15, 2023

(54) PATIENT SUPPORT SYSTEM WITH CHEST COMPRESSION SYSTEM AND HARNESS ASSEMBLY WITH SENSOR SYSTEM

(71) Applicant: Stryker Corporation, Kalamazoo, MI (US)

(72) Inventors: Marko N. Kostic, Johnson City, TN (US); Kurosh Nahavandi, Portage, MI (US); Alexey Titov, Redmond, WA (US); Brandon David Naber, Portage, MI (US); Christopher J. Hopper, Kalamazoo, MI (US); Ming Chen, Ann Arbor, MI (US)

(73) Assignee: Stryker Corporation, Kalamazoo, MI (US)

( * ) Notice: Subject to any disclaimer, the term of this patent is extended or adjusted under 35 U.S.C. 154(b) by 113 days.

This patent is subject to a terminal disclaimer.

(21) Appl. No.: 17/497,065

(22) Filed: Oct. 8, 2021

(65) Prior Publication Data
US 2022/0023144 A1 Jan. 27, 2022

Related U.S. Application Data

(63) Continuation of application No. 16/045,119, filed on Jul. 25, 2018, now Pat. No. 11,179,293.
(Continued)

(51) Int. Cl.
*A61H 31/00* (2006.01)
*A61N 1/04* (2006.01)
(Continued)

(52) U.S. Cl.
CPC ............. *A61H 31/008* (2013.01); *A61G 1/01* (2013.01); *A61G 1/0212* (2013.01);
(Continued)

(58) Field of Classification Search
CPC .... A61H 31/00; A61H 31/004; A61H 31/006; A61H 31/007; A61H 31/008;
(Continued)

(56) References Cited

U.S. PATENT DOCUMENTS 3,046,982 A   7/1962   Davis
3,351,052 A   11/1967  Hewson
(Continued)

FOREIGN PATENT DOCUMENTS

AU   2012216793 A1   10/2012
AU   2013260180 A1   11/2014
(Continued)

OTHER PUBLICATIONS amazon.com, "Evenflo Gold SensorSafe SecueMax Smart Infant Car Seat, Moonstone Webpage", https://www.amazon.com/Evenflo-SensorSafe-SecureMax-Infant-Garnet/dp/B086M382BR?th=1, 1996-2020, 7 pages.
(Continued)

*Primary Examiner* — Justine R Yu
*Assistant Examiner* — Christopher E Miller
(74) *Attorney, Agent, or Firm* — Howard & Howard Attorneys PLLC

(57) ABSTRACT

A patient support system with chest compression system and harness assembly with sensor system. The harness assembly secures shoulders and hips of the patient on a patient support surface during transport. A chest compression system is integrated into the harness assembly in a manner that provides chest compressions to the patient while the patient is secured on the patient support surface. The tension of the harness assembly is selectively adjusted and/or a fluid bladder may be selectively expanded. A controller is in communication with the chest compression system and controls operation of the chest compression system. The
(Continued)

sensor system is integrated into the harness assembly and in communication with the controller. The chest compression system may be removable from the harness assembly via an adapter. The chest compression system may be integrated into the patient support apparatus to secure the patient to the patient support surface while providing chest compressions.

13 Claims, 19 Drawing Sheets

Related U.S. Application Data

(60) Provisional application No. 62/538,452, filed on Jul. 28, 2017.

(51) Int. Cl.
    *A61G 1/044* (2006.01)
    *A61G 1/056* (2006.01)
    *A61G 1/02* (2006.01)
    *A61G 1/01* (2006.01)
    *A61G 1/048* (2006.01)
    *A61N 1/39* (2006.01)
    *G16H 40/63* (2018.01)

(52) U.S. Cl.
    CPC ......... *A61G 1/0237* (2013.01); *A61G 1/0262* (2013.01); *A61G 1/044* (2013.01); *A61G 1/048* (2013.01); *A61G 1/0567* (2013.01); *A61H 31/006* (2013.01); *A61N 1/046* (2013.01); *A61N 1/39044* (2017.08); *A61G 2203/30* (2013.01); *A61G 2203/32* (2013.01); *A61G 2203/34* (2013.01); *A61G 2203/36* (2013.01); *A61G 2203/46* (2013.01); *A61G 2205/30* (2013.01); *A61H 2201/0192* (2013.01); *A61H 2201/105* (2013.01); *A61H 2201/107* (2013.01); *A61H 2201/1616* (2013.01); *A61H 2201/1621* (2013.01); *A61H 2201/1652* (2013.01); *A61H 2201/5007* (2013.01); *A61H 2201/5061* (2013.01); *A61H 2201/5071* (2013.01); *A61H 2201/5082* (2013.01); *A61H 2201/5084* (2013.01); *A61H 2201/5092* (2013.01); *A61H 2230/045* (2013.01); *A61H 2230/201* (2013.01); *A61H 2230/405* (2013.01); *G16H 40/63* (2018.01)

(58) Field of Classification Search
    CPC .. A61H 1/0222; A61H 1/0218; A61H 1/0292; A61G 13/0036; A61G 13/009; A61G 13/0018; A61G 13/10
    See application file for complete search history.

(56) References Cited

U.S. PATENT DOCUMENTS

| | | | |
|---|---|---|---|
| 3,374,783 A | 3/1968 | Hyman | |
| 3,511,275 A | 5/1970 | Hewson | |
| 3,739,771 A | 6/1973 | Gaquer et al. | |
| 3,878,844 A | 4/1975 | Tobias | |
| 3,889,668 A | 6/1975 | Ochs et al. | |
| 3,896,797 A | 7/1975 | Bucur | |
| 4,060,079 A | 11/1977 | Reinhold, Jr. | |
| 4,122,587 A | 10/1978 | Weiss et al. | |
| 4,194,732 A | 3/1980 | Liebman | |
| 4,349,015 A | 9/1982 | Alferness | |
| 4,664,098 A | 5/1987 | Woudenberg et al. | |
| 4,915,095 A | 4/1990 | Chun | |
| 4,928,674 A | 5/1990 | Halperin et al. | |
| 5,014,374 A | 5/1991 | Williams | |
| 5,077,667 A | 12/1991 | Brown et al. | |
| 5,211,186 A | 5/1993 | Shoemaker et al. | |
| 5,362,098 A | 11/1994 | Guill | |
| 5,454,779 A | 10/1995 | Lurie et al. | |
| 5,490,820 A | 2/1996 | Schock et al. | |
| 5,492,285 A | 2/1996 | Hamrick | |
| 5,557,049 A | 9/1996 | Ratner | |
| 5,634,886 A | 6/1997 | Bennett | |
| 5,645,522 A | 7/1997 | Lurie et al. | |
| 5,833,711 A * | 11/1998 | Schneider, Sr. | A61H 31/006 601/151 |
| 5,860,176 A | 1/1999 | Norberg | |
| 5,897,039 A | 4/1999 | Swenke | |
| 5,929,601 A | 7/1999 | Kaib et al. | |
| 6,055,988 A | 5/2000 | Perisho | |
| 6,066,106 A | 5/2000 | Sherman et al. | |
| 6,090,056 A | 7/2000 | Bystrom et al. | |
| 6,142,962 A | 11/2000 | Mollenauer et al. | |
| 6,155,257 A | 12/2000 | Lurie et al. | |
| 6,169,387 B1 | 1/2001 | Kaib | |
| 6,174,295 B1 | 1/2001 | Cantrell et al. | |
| 6,213,960 B1 | 4/2001 | Sherman et al. | |
| 6,332,872 B1 | 12/2001 | Young | |
| 6,390,996 B1 | 5/2002 | Halperin et al. | |
| 6,398,744 B2 | 6/2002 | Bystrom et al. | |
| 6,447,465 B1 | 9/2002 | Sherman et al. | |
| 6,599,258 B1 | 7/2003 | Bystrom et al. | |
| 6,648,841 B1 | 11/2003 | Sessler | |
| 6,681,003 B2 | 1/2004 | Linder et al. | |
| 6,782,293 B2 | 8/2004 | Dupelle et al. | |
| D500,554 S | 1/2005 | Brunjes et al. | |
| 6,931,237 B2 | 8/2005 | Miya et al. | |
| 6,939,314 B2 | 9/2005 | Hall et al. | |
| 6,939,315 B2 | 9/2005 | Sherman et al. | |
| 6,988,499 B2 | 1/2006 | Holt et al. | |
| 7,056,295 B2 | 6/2006 | Halperin | |
| 7,056,296 B2 | 6/2006 | Sherman et al. | |
| 7,060,041 B1 | 6/2006 | Weil et al. | |
| 7,211,056 B2 | 5/2007 | Petelenz et al. | |
| 7,220,235 B2 | 5/2007 | Geheb et al. | |
| 7,226,427 B2 | 6/2007 | Steen | |
| 7,406,301 B2 | 7/2008 | Kasahara et al. | |
| 7,720,535 B2 | 5/2010 | Ni et al. | |
| 7,729,757 B2 | 6/2010 | Parascandola et al. | |
| 7,734,344 B2 | 6/2010 | Ideker et al. | |
| 7,905,233 B2 | 3/2011 | Hopper | |
| 8,001,634 B2 | 8/2011 | Ayette et al. | |
| 8,007,451 B2 | 8/2011 | Havardsholm et al. | |
| 8,089,869 B2 | 1/2012 | Kisela et al. | |
| 8,092,404 B2 | 1/2012 | Kelly et al. | |
| 8,092,581 B2 | 1/2012 | Sugiyama et al. | |
| 8,140,154 B2 | 3/2012 | Donnelly et al. | |
| 8,151,388 B2 | 4/2012 | West, III | |
| 8,301,245 B2 | 10/2012 | Garrett et al. | |
| 8,317,519 B1 | 11/2012 | Orlando | |
| 8,321,011 B2 | 11/2012 | Parascandola et al. | |
| 8,408,207 B2 | 4/2013 | Steen et al. | |
| 8,527,043 B2 | 9/2013 | Dupelle et al. | |
| 8,535,251 B1 | 9/2013 | Rao | |
| 8,577,462 B2 | 11/2013 | Dupelle et al. | |
| 8,588,884 B2 | 11/2013 | Hegde et al. | |
| 8,641,647 B2 | 2/2014 | Illindala et al. | |
| 8,657,764 B2 | 2/2014 | King | |
| 8,690,804 B2 | 4/2014 | Nilsson et al. | |
| 8,690,805 B2 | 4/2014 | Sherman et al. | |
| 8,702,633 B2 | 4/2014 | Voss et al. | |
| 8,768,441 B2 | 7/2014 | De Zwart et al. | |
| 8,777,879 B2 | 7/2014 | Johnson | |
| 8,795,208 B2 | 8/2014 | Walker | |
| 8,795,209 B2 | 8/2014 | Herken et al. | |
| 8,808,205 B2 | 8/2014 | Freeman | |
| 8,874,035 B2 | 10/2014 | Sherman et al. | |
| 8,876,742 B2 | 11/2014 | Centen | |
| 8,888,725 B2 | 11/2014 | Parascandola et al. | |
| 8,897,872 B2 | 11/2014 | Sullivan | |
| 8,922,364 B2 | 12/2014 | Freeman et al. | |
| 8,926,538 B2 | 1/2015 | Centen et al. | |
| 8,942,800 B2 | 1/2015 | Thiagrajan et al. | |
| 8,942,803 B1 | 1/2015 | Herken et al. | |
| 8,951,213 B2 | 2/2015 | Butler et al. | |

(56) References Cited

U.S. PATENT DOCUMENTS

| | | |
|---|---|---|
| 8,967,144 B2 | 3/2015 | Lurie et al. |
| 8,979,764 B2 | 3/2015 | Elghazzawi et al. |
| 8,983,588 B2 | 3/2015 | Addison et al. |
| 9,016,283 B2 | 4/2015 | Paulussen et al. |
| 9,028,259 B2 | 5/2015 | Centen et al. |
| 9,084,880 B2 | 7/2015 | Dupelle et al. |
| 9,099,877 B2 | 8/2015 | Banos et al. |
| 9,107,800 B2 | 8/2015 | Sebelius et al. |
| 9,114,059 B2 | 8/2015 | Bogdanowicz et al. |
| 9,119,767 B2 | 9/2015 | Wood |
| 9,119,971 B2 | 9/2015 | Elghazzawi |
| 9,125,793 B2 | 9/2015 | Palazzolo et al. |
| 9,149,411 B2 | 10/2015 | Coleman et al. |
| 9,149,412 B2 | 10/2015 | Faller et al. |
| 9,180,266 B1 | 11/2015 | Sherman et al. |
| 9,180,304 B2 | 11/2015 | Quan et al. |
| 9,198,826 B2 | 12/2015 | Banville et al. |
| 9,204,845 B2 | 12/2015 | Sullivan et al. |
| 9,211,229 B2 | 12/2015 | Illindala |
| 9,213,801 B2 | 12/2015 | Nova et al. |
| 9,220,443 B2 | 12/2015 | Silver et al. |
| 9,220,912 B2 | 12/2015 | Elghazzawi |
| 9,232,040 B2 | 1/2016 | Barash et al. |
| 9,241,666 B2 | 1/2016 | Packer et al. |
| 9,248,304 B2 | 2/2016 | Banville et al. |
| 9,259,543 B2 | 2/2016 | Paradis et al. |
| 9,265,692 B2 | 2/2016 | Aelen et al. |
| 9,283,339 B2 | 3/2016 | Sherman et al. |
| 9,295,605 B2 | 3/2016 | Yurko et al. |
| 9,295,849 B2 | 3/2016 | Elghazzawi et al. |
| 9,320,677 B2 | 4/2016 | Johnson et al. |
| 9,320,678 B2 | 4/2016 | Illindala |
| 9,352,111 B2 | 5/2016 | Lurie et al. |
| 9,358,178 B1 | 6/2016 | Morgan |
| 9,364,625 B2 | 6/2016 | Silver et al. |
| 9,370,462 B2 | 6/2016 | Halsne et al. |
| 9,383,451 B2 | 7/2016 | Johnson |
| 9,402,781 B2 | 8/2016 | Ritter, III et al. |
| 9,427,597 B2 | 8/2016 | Herken |
| 9,445,967 B2 | 9/2016 | Woerlee et al. |
| 9,504,626 B2 | 11/2016 | Illindala |
| 11,523,967 B2 * | 12/2022 | Stemple ............... A61H 31/006 |
| 2001/0047140 A1 | 11/2001 | Freeman |
| 2002/0026131 A1 | 2/2002 | Halperin |
| 2002/0143278 A1 | 10/2002 | Bystrom et al. |
| 2002/0156401 A1 | 10/2002 | Sherman et al. |
| 2002/0169482 A1 | 11/2002 | SerVaas |
| 2002/0177793 A1 | 11/2002 | Sherman et al. |
| 2003/0004445 A1 | 1/2003 | Hall et al. |
| 2003/0095648 A1 | 5/2003 | Kaib et al. |
| 2003/0135139 A1 | 7/2003 | Bassuk et al. |
| 2003/0181834 A1 | 9/2003 | Sebelius et al. |
| 2004/0039420 A1 | 2/2004 | Jayne et al. |
| 2004/0073145 A1 | 4/2004 | Bystrom et al. |
| 2004/0082888 A1 | 4/2004 | Palazzolo et al. |
| 2004/0116969 A1 | 6/2004 | Owen et al. |
| 2004/0162510 A1 | 8/2004 | Jayne et al. |
| 2004/0162585 A1 | 8/2004 | Elghazzawi et al. |
| 2004/0162587 A1 | 8/2004 | Hampton et al. |
| 2004/0215112 A1 | 10/2004 | Mollenauer et al. |
| 2004/0215244 A1 | 10/2004 | Marcovecchio et al. |
| 2004/0230140 A1 | 11/2004 | Steen |
| 2005/0092324 A1 | 5/2005 | Bowden et al. |
| 2005/0137628 A1 | 6/2005 | Young et al. |
| 2005/0197672 A1 | 9/2005 | Freeman |
| 2005/0267536 A1 | 12/2005 | Freeman et al. |
| 2006/0019229 A1 | 1/2006 | Morallee et al. |
| 2006/0058848 A1 | 3/2006 | Piraino et al. |
| 2006/0116613 A1 | 6/2006 | Halperin et al. |
| 2006/0116724 A1 | 6/2006 | Snyder |
| 2006/0129191 A1 | 6/2006 | Sullivan et al. |
| 2006/0142809 A1 | 6/2006 | Kroll et al. |
| 2006/0270952 A1 | 11/2006 | Freeman et al. |
| 2007/0060785 A1 | 3/2007 | Freeman et al. |
| 2007/0213775 A1 | 9/2007 | Snyder |
| 2007/0219588 A1 | 9/2007 | Freeman |
| 2007/0225623 A1 | 9/2007 | Freeman |
| 2007/0241863 A1 | 10/2007 | Udagawa et al. |
| 2007/0276299 A1 | 11/2007 | Jiang et al. |
| 2007/0276300 A1 | 11/2007 | Olson et al. |
| 2007/0299473 A1 | 12/2007 | Matos |
| 2008/0097257 A1 | 4/2008 | Stromsnes |
| 2008/0097534 A1 | 4/2008 | Myklebust et al. |
| 2008/0125821 A1 | 5/2008 | Blomquist |
| 2008/0208070 A1 | 8/2008 | Snyder et al. |
| 2008/0215102 A1 | 9/2008 | Myklebust et al. |
| 2008/0215103 A1 | 9/2008 | Powers |
| 2008/0242916 A1 | 10/2008 | Avni |
| 2008/0255482 A1 | 10/2008 | Lurie |
| 2008/0269030 A1 | 10/2008 | Hoffman et al. |
| 2008/0298330 A1 | 12/2008 | Leitch |
| 2008/0300518 A1 | 12/2008 | Bowes |
| 2008/0312565 A1 | 12/2008 | Celik-Butler et al. |
| 2008/0312708 A1 | 12/2008 | Snyder |
| 2008/0319359 A1 | 12/2008 | Moomiaie-Qajar et al. |
| 2009/0270931 A1 | 10/2009 | Liden |
| 2009/0277447 A1 | 11/2009 | Voss et al. |
| 2010/0004571 A1 | 1/2010 | Nilsson et al. |
| 2010/0004710 A1 | 1/2010 | Kellum |
| 2010/0022886 A1 | 1/2010 | Ayati et al. |
| 2010/0198118 A1 | 8/2010 | Itnati |
| 2010/0211127 A1 | 8/2010 | Eerden |
| 2010/0228166 A1 | 9/2010 | Centen |
| 2010/0234908 A1 | 9/2010 | Didon |
| 2010/0326442 A1 | 12/2010 | Hamilton et al. |
| 2011/0040217 A1 | 2/2011 | Centen |
| 2011/0066089 A1 | 3/2011 | Udassi et al. |
| 2011/0092864 A1 | 4/2011 | Woerlee et al. |
| 2011/0098611 A1 | 4/2011 | Flood |
| 2011/0105930 A1 | 5/2011 | Thiagarajan et al. |
| 2011/0112423 A1 | 5/2011 | Chapman et al. |
| 2011/0117529 A1 | 5/2011 | Barash et al. |
| 2011/0117878 A1 | 5/2011 | Barash et al. |
| 2011/0166490 A1 | 7/2011 | Woerlee et al. |
| 2011/0172550 A1 | 7/2011 | Martin et al. |
| 2011/0218467 A1 | 9/2011 | Hsu |
| 2011/0237959 A1 | 9/2011 | Van Houwelingen |
| 2011/0245704 A1 | 10/2011 | Monsieurs et al. |
| 2011/0295078 A1 | 12/2011 | Reid et al. |
| 2012/0083720 A1 | 4/2012 | Centen et al. |
| 2012/0123223 A1 | 5/2012 | Freeman et al. |
| 2012/0123242 A1 | 5/2012 | Stilley et al. |
| 2012/0184882 A1 | 7/2012 | Totman et al. |
| 2012/0191476 A1 | 7/2012 | Reid et al. |
| 2012/0203147 A1 | 8/2012 | Lurie et al. |
| 2012/0238922 A1 | 9/2012 | Stemple et al. |
| 2012/0255124 A1 | 10/2012 | West |
| 2012/0259156 A1 | 10/2012 | Freeman |
| 2012/0260428 A1 | 10/2012 | Franklin |
| 2012/0310123 A1 | 12/2012 | Mossmer |
| 2013/0023781 A1 | 1/2013 | Freeman et al. |
| 2013/0030333 A1 | 1/2013 | Cicenas et al. |
| 2013/0096649 A1 | 4/2013 | Martin et al. |
| 2013/0132465 A1 | 5/2013 | Brown |
| 2013/0150759 A1 | 6/2013 | Nitta |
| 2013/0218056 A1 | 8/2013 | Aelen et al. |
| 2013/0226255 A1 | 8/2013 | Chapman et al. |
| 2013/0231711 A1 | 9/2013 | Kaib |
| 2013/0282068 A1 | 10/2013 | Sagiroglu et al. |
| 2013/0282069 A1 | 10/2013 | Thiagarajan et al. |
| 2013/0282072 A1 | 10/2013 | Abdeen et al. |
| 2013/0296747 A1 | 11/2013 | Perreault et al. |
| 2013/0310718 A1 | 11/2013 | Jensen et al. |
| 2013/0324873 A1 | 12/2013 | Babaeizadeh et al. |
| 2014/0002241 A1 | 1/2014 | Elghazzawi |
| 2014/0004814 A1 | 1/2014 | Elghazzawi |
| 2014/0005506 A1 | 1/2014 | Elghazzawi |
| 2014/0031883 A1 | 1/2014 | Elghazzawi |
| 2014/0039359 A1 | 2/2014 | Madanat |
| 2014/0046227 A1 | 2/2014 | Fleming |
| 2014/0046228 A1 | 2/2014 | Walker |
| 2014/0047314 A1 | 2/2014 | Esibov et al. |
| 2014/0052032 A1 | 2/2014 | Freeman et al. |
| 2014/0057235 A1 | 2/2014 | Kellum et al. |

(56) References Cited

U.S. PATENT DOCUMENTS

| | | |
|---|---|---|
| 2014/0060546 A1 | 3/2014 | Pino et al. |
| 2014/0093135 A1 | 4/2014 | Reid et al. |
| 2014/0100496 A1 | 4/2014 | Johnson et al. |
| 2014/0121576 A1 | 5/2014 | Nilsson et al. |
| 2014/0135668 A1 | 5/2014 | Belalcazar |
| 2014/0155792 A1 | 6/2014 | Karve et al. |
| 2014/0171839 A1 | 6/2014 | Fleming |
| 2014/0171840 A1 | 6/2014 | Aelen et al. |
| 2014/0180180 A1 | 6/2014 | Nilsson et al. |
| 2014/0188500 A1 | 7/2014 | Chapman et al. |
| 2014/0201627 A1 | 7/2014 | Freeman et al. |
| 2014/0207371 A1 | 7/2014 | Johnson |
| 2014/0213942 A1 | 7/2014 | Hanson |
| 2014/0221882 A1 | 8/2014 | Jeppsson |
| 2014/0221883 A1 | 8/2014 | Jeppsson |
| 2014/0236053 A1 | 8/2014 | Walker et al. |
| 2014/0236055 A1 | 8/2014 | Woerlee et al. |
| 2014/0276269 A1 | 9/2014 | Illindala |
| 2014/0292534 A1 | 10/2014 | Stever et al. |
| 2014/0323928 A1 | 10/2014 | Johnson |
| 2014/0336546 A1 | 11/2014 | Chapman et al. |
| 2014/0337047 A1 | 11/2014 | Mears et al. |
| 2014/0342330 A1 | 11/2014 | Freeman et al. |
| 2014/0378782 A1 | 12/2014 | Herken et al. |
| 2015/0005588 A1 | 1/2015 | Herken et al. |
| 2015/0031961 A1 | 1/2015 | Freeman |
| 2015/0035654 A1 | 2/2015 | Kaib et al. |
| 2015/0045697 A1 | 2/2015 | Richard et al. |
| 2015/0051521 A1 | 2/2015 | Woerlee et al. |
| 2015/0052376 A1 | 2/2015 | Volpe et al. |
| 2015/0079568 A1 | 3/2015 | Duval-Arould et al. |
| 2015/0087919 A1 | 3/2015 | Johnson et al. |
| 2015/0088016 A1 | 3/2015 | Fleischacker et al. |
| 2015/0094625 A1 | 4/2015 | Freeman et al. |
| 2015/0094626 A1 | 4/2015 | Jones et al. |
| 2015/0105636 A1 | 4/2015 | Hayman et al. |
| 2015/0105637 A1 | 4/2015 | Yu et al. |
| 2015/0109125 A1 | 4/2015 | Kaib et al. |
| 2015/0119768 A1 | 4/2015 | Meier et al. |
| 2015/0164339 A1 | 6/2015 | Xu et al. |
| 2015/0164417 A1 | 6/2015 | Tupin, Jr. |
| 2015/0165223 A1 | 6/2015 | Babaeizadeh et al. |
| 2015/0170546 A1 | 6/2015 | Kirenko |
| 2015/0178457 A1 | 6/2015 | Grimley et al. |
| 2015/0182419 A1 | 7/2015 | Clowdus |
| 2015/0213212 A1 | 7/2015 | Grimley et al. |
| 2015/0224022 A1 | 8/2015 | Hanson |
| 2015/0231026 A1 | 8/2015 | Lurie |
| 2015/0231028 A1 | 8/2015 | Belalcazar |
| 2015/0257971 A1 | 9/2015 | Chapman et al. |
| 2015/0265497 A1 | 9/2015 | Kaufman et al. |
| 2015/0272822 A1 | 10/2015 | Wik et al. |
| 2015/0285696 A1 | 10/2015 | Adamski et al. |
| 2015/0297107 A1 | 10/2015 | Sullivan et al. |
| 2015/0302555 A1 | 10/2015 | Paulussen et al. |
| 2015/0313493 A1 | 11/2015 | Sullivan |
| 2015/0313778 A1 | 11/2015 | Chia et al. |
| 2015/0327777 A1 | 11/2015 | Kostic et al. |
| 2015/0327807 A1 | 11/2015 | Bronner et al. |
| 2015/0328083 A1 | 11/2015 | Delisle et al. |
| 2015/0328417 A1 | 11/2015 | Loser et al. |
| 2015/0343227 A1 | 12/2015 | Elghazzawi |
| 2015/0351647 A1 | 12/2015 | Dantu et al. |
| 2015/0352002 A1 | 12/2015 | Jeppsson et al. |
| 2015/0352369 A1 | 12/2015 | Quan et al. |
| 2016/0015991 A1 | 1/2016 | Firoozabadi et al. |
| 2016/0051780 A1 | 2/2016 | Sherman et al. |
| 2016/0058660 A1 | 3/2016 | Lurie et al. |
| 2016/0095765 A1 | 4/2016 | Ehrstedt et al. |
| 2016/0095782 A1 | 4/2016 | Shockley, Jr. et al. |
| 2016/0098935 A1 | 4/2016 | Duval-Arnould et al. |
| 2016/0100302 A1 | 4/2016 | Barash et al. |
| 2016/0106362 A1 | 4/2016 | Packer et al. |
| 2016/0128626 A1 | 5/2016 | Johnson et al. |
| 2016/0128898 A1 | 5/2016 | Hagl et al. |
| 2016/0128899 A1 | 5/2016 | Lurie et al. |
| 2016/0133160 A1 | 5/2016 | Packer et al. |
| 2016/0136042 A1 | 5/2016 | Nilsson et al. |
| 2016/0143804 A1 | 5/2016 | Nilsson et al. |
| 2016/0143805 A1 | 5/2016 | Aelen |
| 2016/0151592 A1 | 6/2016 | Sherman et al. |
| 2016/0175602 A1 | 6/2016 | Aoyama et al. |
| 2016/0187153 A1 | 6/2016 | Johnson |
| 2016/0196387 A1 | 7/2016 | Whannel et al. |
| 2016/0213559 A1 | 7/2016 | Schiller et al. |
| 2016/0213560 A1 | 7/2016 | Sturdivant |
| 2016/0213942 A1 | 7/2016 | Elghazzawi et al. |
| 2016/0225290 A1 | 8/2016 | Barash et al. |
| 2016/0242996 A1 | 8/2016 | von Schenck et al. |
| 2016/0253471 A1 | 9/2016 | Volpe |
| 2016/0256102 A1 | 9/2016 | Castiel et al. |
| 2016/0274162 A1 | 9/2016 | Freeman et al. |
| 2016/0278652 A1 | 9/2016 | Kaib et al. |
| 2016/0283900 A1 | 9/2016 | Johnson et al. |
| 2016/0287470 A1 | 10/2016 | Lewis et al. |
| 2016/0294951 A1 | 10/2016 | Durrant et al. |
| 2016/0338886 A1 | 11/2016 | Schroeder et al. |
| 2017/0258677 A1 | 9/2017 | Lurie et al. |
| 2018/0008510 A1 | 1/2018 | Lurie et al. |
| 2018/0110667 A1 | 4/2018 | Freeman et al. |
| 2018/0133103 A1 | 5/2018 | Lurie |
| 2018/0333328 A1 | 11/2018 | Lurie et al. |
| 2019/0008720 A1 | 1/2019 | Joshi et al. |
| 2019/0029920 A1 | 1/2019 | Kostic et al. |
| 2020/0121552 A1 | 4/2020 | Reynolds et al. |

FOREIGN PATENT DOCUMENTS

| | | |
|---|---|---|
| CA | 2097355 C | 7/1999 |
| CA | 2327902 A1 | 6/2002 |
| CA | 2538482 A1 | 8/2007 |
| CA | 2670032 A1 | 12/2010 |
| CN | 2276790 Y | 3/1998 |
| CN | 2326237 Y | 6/1999 |
| CN | 2482996 Y | 3/2002 |
| CN | 201366067 Y | 12/2009 |
| CN | 101744714 A | 6/2010 |
| CN | 201542908 U | 8/2010 |
| CN | 201572307 U | 9/2010 |
| CN | 101933882 A | 1/2011 |
| CN | 202236214 U | 5/2012 |
| CN | 202342427 U | 7/2012 |
| CN | 103584993 A | 2/2014 |
| CN | 203815857 U | 9/2014 |
| CN | 104352345 A | 2/2015 |
| CN | 104434493 A | 3/2015 |
| CN | 204274975 U | 4/2015 |
| CN | 204618817 U | 9/2015 |
| CN | 105078732 A | 11/2015 |
| CN | 105079931 A | 11/2015 |
| CN | 105125190 A | 12/2015 |
| CN | 105213166 A | 1/2016 |
| CN | 105287187 A | 2/2016 |
| CN | 105411832 A | 3/2016 |
| CN | 104434493 B | 5/2016 |
| CN | 105796087 A | 7/2016 |
| DE | 4133637 A1 | 4/1993 |
| DE | 69427906 T2 | 4/2002 |
| DE | 102012024672 A1 | 6/2014 |
| EP | 0688201 B1 | 8/2001 |
| EP | 1667767 A1 | 6/2006 |
| EP | 2883496 A1 | 6/2015 |
| EP | 2893955 A1 | 7/2015 |
| EP | 2946762 A1 | 11/2015 |
| EP | 2952170 A1 | 12/2015 |
| EP | 3037127 A1 | 6/2016 |
| GB | 2458389 A | 9/2009 |
| GB | 2460690 A | 12/2009 |
| GB | 2465817 A | 6/2010 |
| IN | 2010MN02319 A | 3/2011 |
| IN | 750DEL2011 A | 11/2012 |
| IN | 8693CHENP2012 A | 4/2016 |
| JP | 3510254 B2 | 3/2004 |
| KR | 20140119953 A | 10/2014 |

(56) References Cited

FOREIGN PATENT DOCUMENTS

| | | |
|---|---|---|
| KR | 101529299 B1 | 6/2015 |
| KR | 20160063207 A | 6/2016 |
| KR | 20160080030 A | 7/2016 |
| SE | 0100616 L | 8/2002 |
| TW | I244929 B | 12/2005 |
| WO | 9420060 A1 | 9/1994 |
| WO | 9628128 A1 | 9/1996 |
| WO | 9724062 A1 | 7/1997 |
| WO | 9731608 A1 | 9/1997 |
| WO | 9909929 A1 | 3/1999 |
| WO | 9924114 A1 | 5/1999 |
| WO | 9947028 A1 | 9/1999 |
| WO | 0030712 A1 | 6/2000 |
| WO | 2005021089 A1 | 3/2005 |
| WO | 2008084464 A1 | 7/2008 |
| WO | 2008144862 A2 | 12/2008 |
| WO | 2010059049 A2 | 5/2010 |
| WO | 2010098892 A2 | 9/2010 |
| WO | 2012075493 A1 | 6/2012 |
| WO | 2012100219 A1 | 7/2012 |
| WO | 2013169346 A1 | 11/2013 |
| WO | 2014003946 A1 | 1/2014 |
| WO | 2014003947 A2 | 1/2014 |
| WO | 2014003948 A1 | 1/2014 |
| WO | 2014018157 A1 | 1/2014 |
| WO | 2014018158 A1 | 1/2014 |
| WO | 2014018160 A1 | 1/2014 |
| WO | 2014052802 A3 | 4/2014 |
| WO | 2014092994 A1 | 6/2014 |
| WO | 2014110280 A3 | 7/2014 |
| WO | 2014137727 A1 | 9/2014 |
| WO | 2014160838 A1 | 10/2014 |
| WO | 2014182649 A1 | 11/2014 |
| WO | 2014210510 A1 | 12/2014 |
| WO | 2015017718 A1 | 2/2015 |
| WO | 2015022387 A1 | 2/2015 |
| WO | 2015047867 A1 | 4/2015 |
| WO | 2015048528 A4 | 4/2015 |
| WO | 2015074015 A1 | 5/2015 |
| WO | 2015075691 A1 | 5/2015 |
| WO | 2015075696 A1 | 5/2015 |
| WO | 2015082318 A1 | 6/2015 |
| WO | 2015095729 A1 | 6/2015 |
| WO | 2015101878 A1 | 7/2015 |
| WO | 2015101911 A1 | 7/2015 |
| WO | 2015123198 A1 | 8/2015 |
| WO | 2015175578 A1 | 11/2015 |
| WO | 2016007471 A1 | 1/2016 |
| WO | 2016077786 A1 | 5/2016 |
| WO | 2016081381 A1 | 5/2016 |
| WO | 2016091948 A1 | 6/2016 |
| WO | 2016092477 A1 | 6/2016 |
| WO | 2016092480 A1 | 6/2016 |
| WO | 2016097934 A1 | 6/2016 |
| WO | 2016097938 A1 | 6/2016 |
| WO | 2016100706 A1 | 6/2016 |
| WO | 2016106132 A2 | 6/2016 |
| WO | 2016106132 A3 | 6/2016 |
| WO | 2016109393 A1 | 7/2016 |
| WO | 2016109855 A1 | 7/2016 |
| WO | 2016138240 A1 | 9/2016 |
| WO | 2016154274 A2 | 9/2016 |
| WO | 2016160369 A1 | 10/2016 |
| WO | 2016160841 A1 | 10/2016 |
| WO | 2016160849 A1 | 10/2016 |
| WO | 2016160851 A1 | 10/2016 |

OTHER PUBLICATIONS

Condliffe, Jamie, "This Tiny Patch Keeps Track of Your Heart and Body Chemistry at Once", May 23, 2016, 1 page, http://gizmodo.com/this-tiny-patch-keeps-track-of-your-heart-and-body-chem-1778146432.

English language abstract and machine-assisted English translation for CN 101744714 extracted from espacenet.com database on Sep. 13, 2018, 15 pages.

English language abstract and machine-assisted English translation for CN 101933882 extracted from espacenet.com database on Sep. 13, 2018, 11 pages.

English language abstract and machine-assisted English translation for CN 103584993 extracted from espacenet.com database on Sep. 13, 2018, 6 pages.

English language abstract and machine-assisted English translation for CN 104352345 extracted from espacenet.com database on Sep. 13, 2018, 12 pages.

English language abstract and machine-assisted English translation for CN 104434493 extracted from espacenet.com database on Sep. 13, 2018, 9 pages.

English language abstract and machine-assisted English translation for CN 104434493A extracted from espacenet.com database on Sep. 13, 2018, 9 pages.

English language abstract and machine-assisted English translation for CN 104434493B extracted from espacenet.com database on Sep. 13, 2018, 9 pages.

English language abstract and machine-assisted English translation for CN 105078732 extracted from espacenet.com database on Sep. 13, 2018, 12 pages.

English language abstract and machine-assisted English translation for CN 105125190 extracted from espacenet.com database on Sep. 13, 2018, 13 pages.

English language abstract and machine-assisted English translation for CN 105213166 extracted from espacenet.com database on Sep. 13, 2018, 8 pages.

English language abstract and machine-assisted English translation for CN 105287187 extracted from espacenet.com database on Sep. 13, 2018, 10 pages.

English language abstract and machine-assisted English translation for CN 105411832 extracted from espacenet.com database on Sep. 13, 2018, 9 pages.

English language abstract and machine-assisted English translation for CN 105796087 extracted from espacenet.com database on Sep. 13, 2018, 11 pages.

English language abstract and machine-assisted English translation for CN 201366067 extracted from espacenet.com database on Sep. 13, 2018, 11 pages.

English language abstract and machine-assisted English translation for CN 201542908 extracted from espacenet.com database on Sep. 13, 2018, 7 pages.

English language abstract and machine-assisted English translation for CN 201572307 extracted from espacenet.com database on Sep. 13, 2018, 9 pages.

English language abstract and machine-assisted English translation for CN 202236214 extracted from espacenet.com database on Sep. 13, 2018, 10 pages.

English language abstract and machine-assisted English translation for CN 202342427 extracted from espacenet.com database on Sep. 13, 2018, 6 pages.

English language abstract and machine-assisted English translation for CN 203815857 extracted from espacenet.com database on Sep. 13, 2018, 11 pages.

English language abstract and machine-assisted English translation for CN 204274975 extracted from espacenet.com database on Sep. 13, 2018, 8 pages.

English language abstract and machine-assisted English translation for CN 204618817 extracted from espacenet.com database on Sep. 13, 2018, 8 pages.

English language abstract and machine-assisted English translation for CN 2276790 extracted from espacenet.com database on Sep. 13, 2018, 5 pages.

English language abstract and machine-assisted English translation for CN 2326237 extracted from espacenet.com database on Sep. 13, 2018, 7 pages.

English language abstract and machine-assisted English translation for CN 2482996 extracted from espacenet.com database on Sep. 13, 2018, 15 pages.

(56) References Cited

OTHER PUBLICATIONS

English language abstract and machine-assisted English translation for DE 41 33 637 extracted from espacenet.com database on Sep. 13, 2018, 8 pages.

English language abstract and machine-assisted English translation for KR 10-1529299 extracted from espacenet.com database on Sep. 13, 2018, 15 pages.

English language abstract and machine-assisted English translation for KR 2014-0119953 extracted from espacenet.com database on Sep. 13, 2018, 17 pages.

English language abstract and machine-assisted English translation for KR 2016-0063207 extracted from espacenet.com database on Sep. 13, 2018, 9 pages.

English language abstract and machine-assisted English translation for KR 2016-0080030 extracted from espacenet.com database on Sep. 13, 2018, 16 pages.

English language abstract for CN 105079931 extracted from espacenet.com database on Sep. 13, 2018, 1 page.

English language abstract for DE 10 2012 024 672 extracted from espacenet.com database on Sep. 13, 2018, 2 pages.

English language abstract for DE 694 27 906 extracted from espacenet.com database on Sep. 13, 2018, 2 pages.

English language abstract for JP 3510254 extracted from espacenet.com database on Sep. 13, 2018, 2 pages.

English language abstract for SE 0100616 extracted from espacenet.com database on Sep. 13, 2018, 1 page.

English language abstract for TWI 244929 extracted from espacenet.com database on Sep. 13, 2018, 1 page.

Erich, John, "Heads-Up CPR: Can Elevating the Patient's Head Improve Outcomes?", EMS World, May 27, 2015, 2 pages, http://www.emsworld.com/article/12078215/heads-up-cpr.

Imani, Somayeh et al., "A Wearable Chemical-Electrophysiological Hybrid Biosensing System for Real-Time Health and Fitness Monitoring", May 23, 2016, pp. 1-7.

Physio Control, "LUCAS Chest Compression System Brochure", 2012, 16 pages.

Queensland Ambulance Service, "Clinical Practice Procedures: Cardiac/Mechanical Chest Compression Device—Corpuls CPR", https://www.ambulance.qld.gov.au/docs/clinical/cpp/CPP_Chest%20compression%20device_corpuls.pdf, 2020, 7 pages.

Zephyr Technology Corporation, "Zephyr PSM Responder Brochure", 2016, 11 pages.

Zephyr Technology Corporation, "BioHarness 3, Model BH3 Webpage", 2016, 2 pages, https://www.zephyranywhere.com/products/bioharness-3.

Zephyr Technology Corporation, "HxM Smart Heart Rate Monitor Webpage", 2016, 2 pages, https://www.zephyranywhere.com/products/hxm-smart-heart-rate-monitor.

Zephyr Technology Corporation, "OmniSense Software Webpage", 2016, 5 pages, https://www.zephyranywhere.com/products/omnisense-software.

Zoll Medical Corporation, "AutoPulse—The System for High-Quality CPR", 2015, 5 pages.

\* cited by examiner

PATIENT SUPPORT SYSTEM WITH CHEST COMPRESSION SYSTEM AND HARNESS ASSEMBLY WITH SENSOR SYSTEM

CROSS REFERENCE TO RELATED APPLICATIONS

This application is a Continuation of U.S. patent application Ser. No. 16/045,119, filed on Jul. 25, 2018, which claims priority to and the benefit of U.S. Provisional Patent Application No. 62/538,452, filed on Jul. 28, 2017, the disclosures of each of which are hereby incorporated by reference in their entirety.

BACKGROUND

Patient support apparatuses, such as hospital beds, stretchers, cots, and tables, facilitate care of patients in a health care setting, and typically comprise a patient support surface supported by a base. Facilitation of care often requires transporting the patient positioned supine on the patient support surface. During transport, it is critical that the patient remain situated on the patient support surface to avoid injury, and preferably immobilized to receive uncompromised treatment from attending caregivers.

Although casual transport of the patient on a hospital bed through a hospital corridor is generally routine and uneventful, emergency scenarios arise that require securing the patient to the patient support apparatus. One exemplary scenario includes transporting the patient on an ambulance cot in an ambulance during a medical emergency. First responders arrive on the scene of the medical emergency and must timely remove and transport the patient to the next point of definitive care, most likely the emergency department at a hospital. The exigent circumstances of the medical emergency heighten the risk of accident or patient mishandling. One obvious circumstance includes the extremely high speeds at which the ambulance is traveling in route to the hospital.

Consequently, restraint straps are commonly used to secure the patient to the ambulance cot or other patient support apparatus. Often, three or more restraint straps extend transversely across the ambulance cot and are longitudinally spaced from a head end to a foot end. A buckle removably secures counterpart portions of each strap. Sometimes, the straps are uncomfortable for the patient (e.g., painful pressure points). Further, the straps may be cumbersome to the first responders, often becoming lodged within various mechanisms of the ambulance cot and/or dragging on the ground. Still further, despite recommended procedures for securing the patient to the patient support surface (in the event of a sudden stop or vehicle collision), the design of the straps themselves often discourage adherence to such procedures. Still further yet, the straps forego an opportunity to comprise a functional component of the patient support apparatus.

A patient support system designed to overcome one or more of the aforementioned disadvantages is desired.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
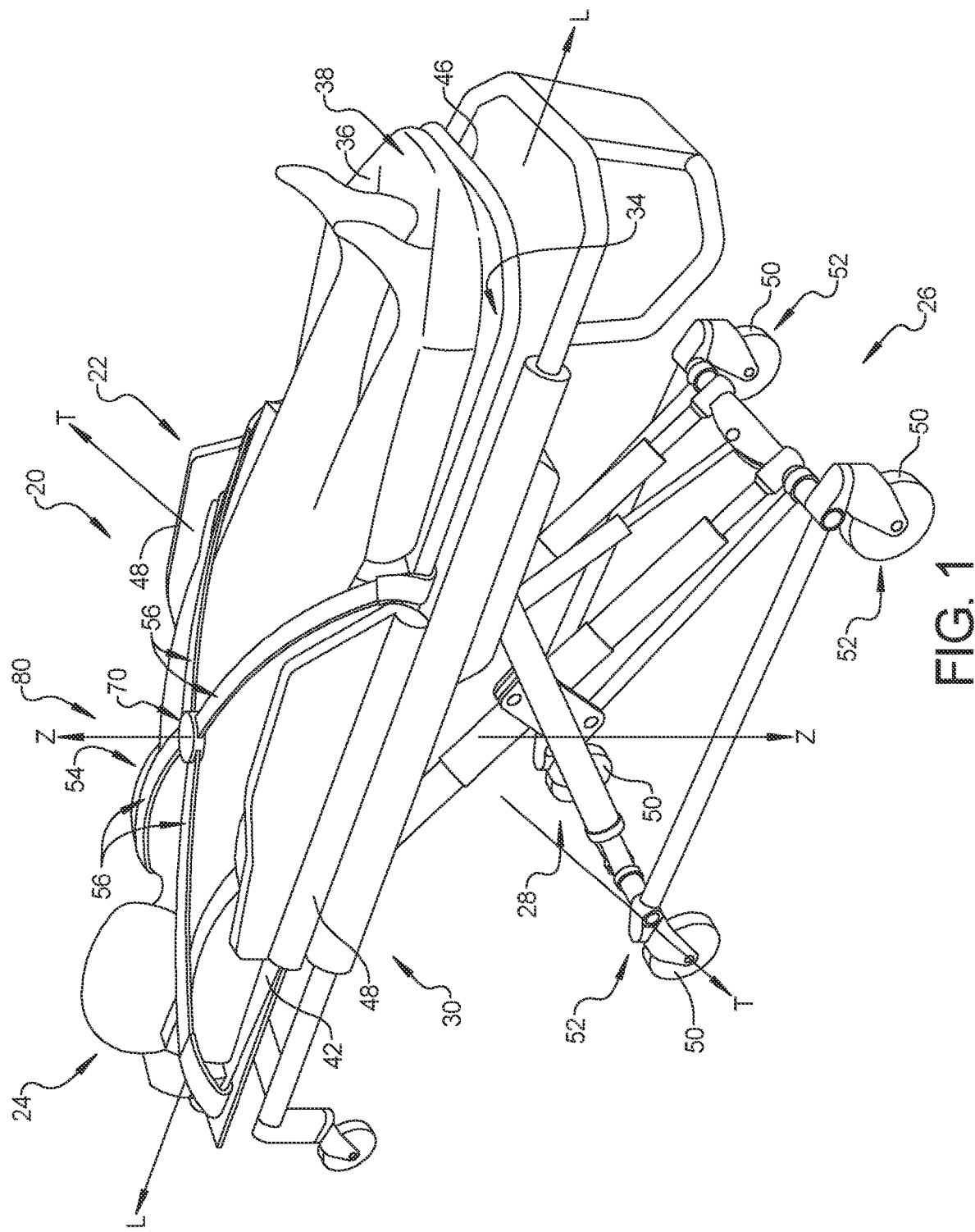
FIG. 1 is a perspective view of a patient support system in accordance with an exemplary embodiment of the present disclosure with the patient support system comprising a harness assembly and a chest compression system.

FIG. 1 illustrates a patient support system 20 in accordance with an exemplary embodiment. The patient support system 20 comprises a patient support apparatus 22 configured to support a patient 24 above a surface during transport. The patient support apparatus 22 of FIG. 1 is an ambulance cot supporting the patient 24 in a supine position above a floor surface. Exemplary ambulance cots that may comprise the patient support apparatus 22 are models Power-PRO™ XT, Power-PRO™ IT, Performance-PRO™ XT, Power-PRO™ TL, MX-PRO® R3, MX-PRO® Bariatric Transport, and the M-1® Roll-in System, each from Stryker Corporation (Kalamazoo, Mich.), or other types of cots. In still other embodiments, the patient support apparatus 22 may comprise a hospital bed, stretcher, or similar apparatus utilized in the transport of a patient generally positioned in the supine, incline, and/or decline positions.

The patient support apparatus 22 comprises a base 26 and an intermediate support assembly 28. The intermediate support assembly 28 is disposed above and coupled to the base 26 as shown in FIG. 1. The intermediate support assembly 28 generally comprises frame members and actuators configured to raise or lower the patient 24 supported on a patient support deck 34. In the exemplary embodiment of FIG. 1, raising or lowering of the patient support deck 34 relative to the base 26 results in a scissor-like motion of the intermediate support assembly 28. The construction of the base 26 and/or the intermediate support assembly 28 may take on any known or conventional design, and is not limited to that specifically set forth above.

Figure 2A:
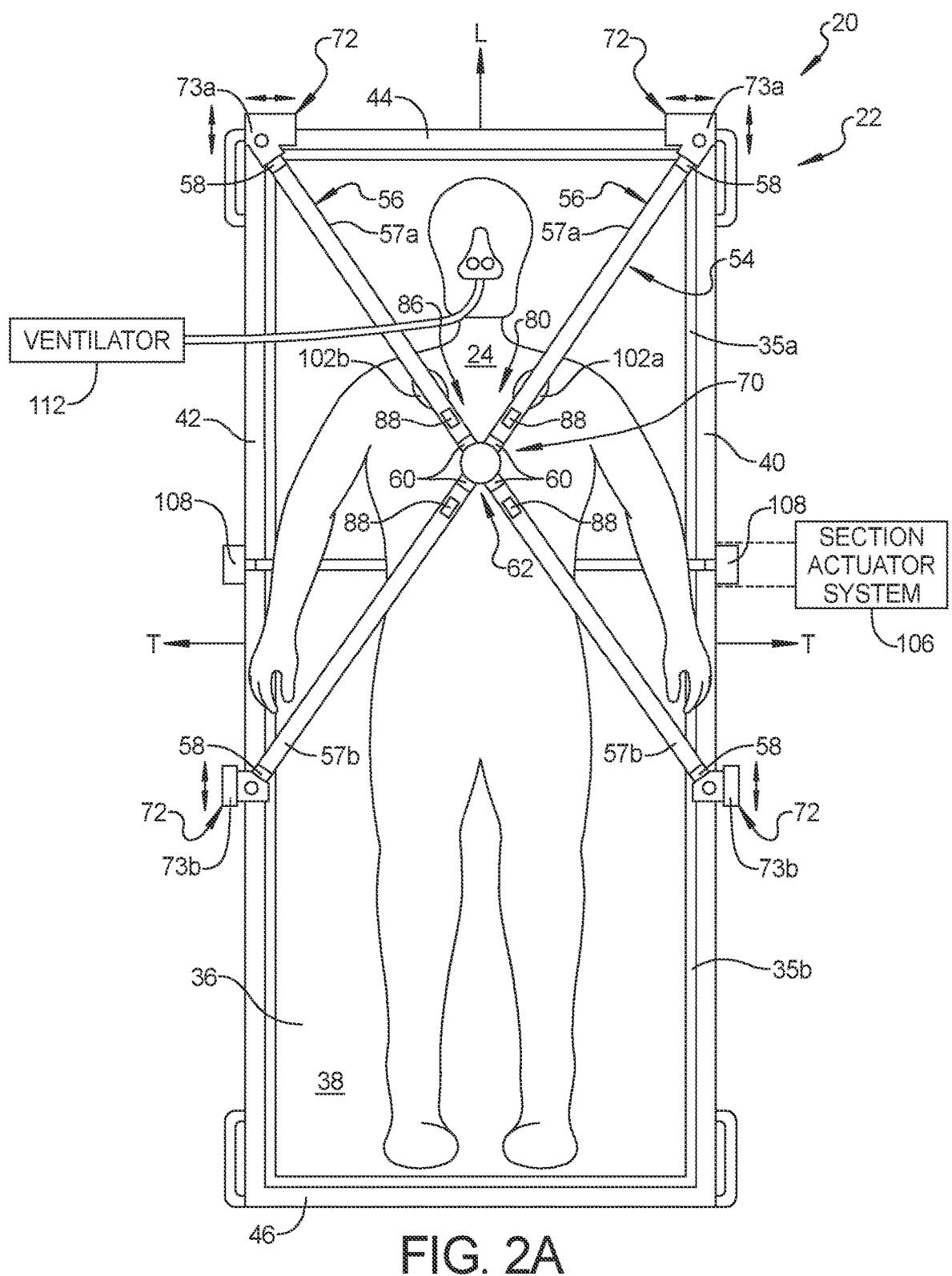
FIG. 2A is a top plan view of the patient support system of FIG. 1.
Figure 2B:
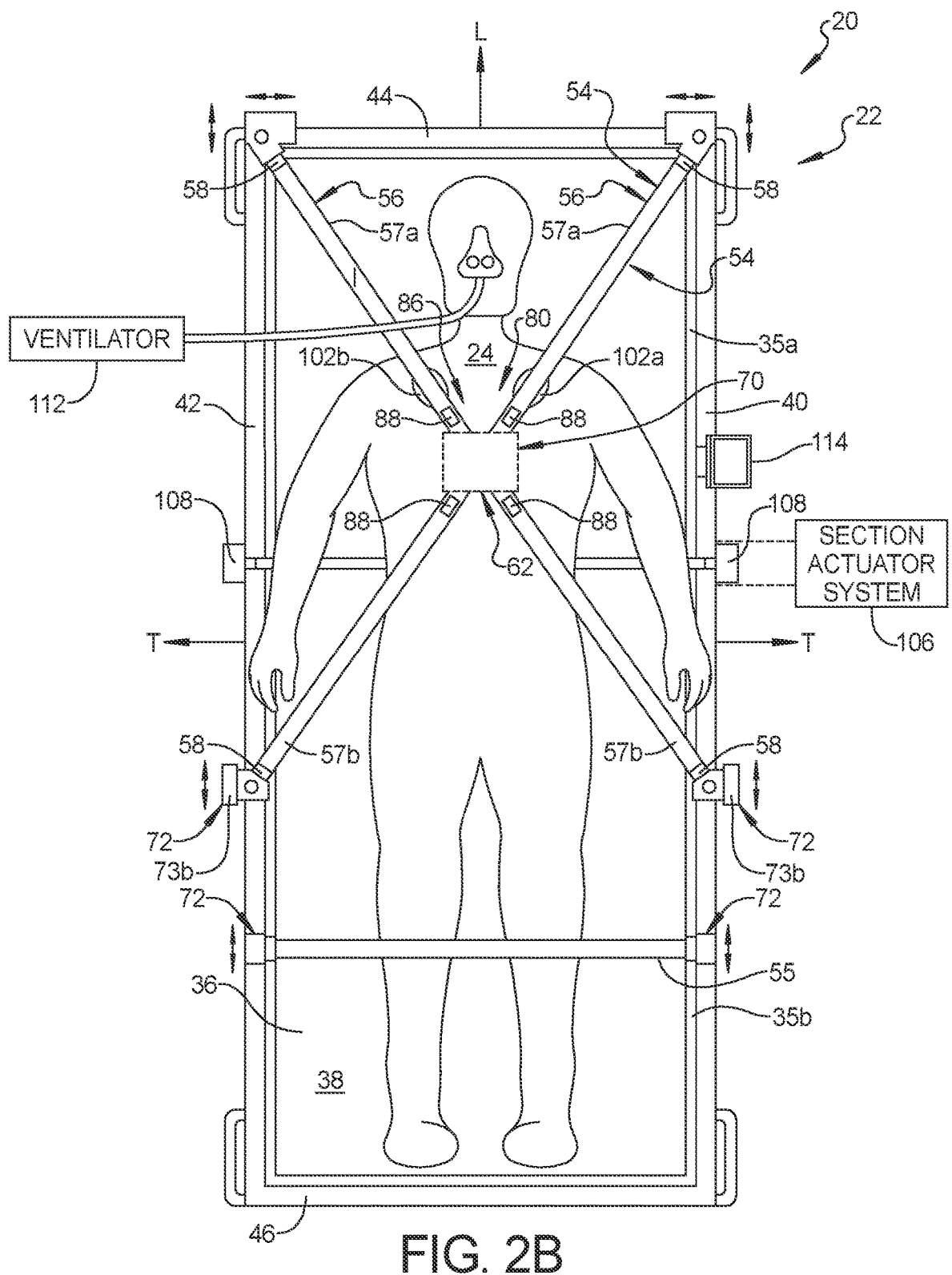
FIG. 2B is a top plan view of a patient support system in accordance with another exemplary embodiment of the present disclosure with the patient support system comprising a harness assembly and a chest compression system. A junction of the harness assembly is represented schematically.

A support frame 30 is coupled to and positioned above the intermediate support assembly 28. The support frame 30 comprises the patient support deck 34. The support frame 30 is configured to support the patient 24 relative to the intermediate support assembly 28. The support frame 30 and/or patient support deck 34 may comprise one or more sections, some of which may be movable relative to the intermediate support assembly 28, such as a fowler section, a seat section, a thigh section, and/or foot section. FIGS. 2A and 2B schematically illustrate two sections—a fowler section 35a generally supporting the patient's upper body, and a seat section 35b generally supporting the patient's lower body. One or more of the movable sections 35a, 35b is configured to articulate relative to another one of the movable sections 35a, 35b, the intermediate support assembly 28, or other structure of the patient support apparatus 22. In one example, movable sections 35a, 35b are articulated via one or more actuators 108 of a section actuator system 106. As discussed below, the section actuator system 106 may be coupled to the movable sections 35a, 35b. The section actuator system 106 may be coupled to the intermediate support assembly 28, the support frame 30, and/or the support patient support deck 34 and configured to control movement of the fowler section 35a and/or the seat section 35b relative to one another and/or to the base 26. In other exemplary embodiments, the patient support deck 34 comprises a rigid panel without movable sections.

The support frame 30 may further comprise frame rails 40, 42, 44, 46 supported by the intermediate support assembly 28 and/or base 26. A first frame rail 40 is positioned at a right side of the patient support deck 34 when viewed in plan (FIGS. 2A and 2B). A second frame rail 42 is positioned at a left side of the patient support deck 34 when viewed in plan. A third frame rail 44 is positioned at the head end of the patient support deck 34. A fourth frame rail 46 is positioned at the foot end of the patient support deck 34. The support frame 30, and more particularly the frame rails 40, 42, 44, 46, may directly or indirectly support the patient support deck 34 through suitable structural members, couplings or connection means.

The frame rails 40, 42, 44, 46 may be arranged in a substantially rectangular configuration and generally contoured to the patient support deck 34. The frame rails 40, 42, 44, 46 may be comprised of four discrete structures coupled together at their respective ends and/or along their respective lengths. The present disclosure contemplates there may be greater or fewer than four frame rails. For example, two L-shaped rails may be coupled to comprise the substantially rectangular configuration. Further, the frame rails may form one continuous loop; however, any suitable construction of the support frame 30 may be employed, including constructions lacking any frame rails.

A mattress 36 is typically disposed on the patient support deck 34 during use. The mattress 36 directly supports the patient 24 disposed thereupon. The mattress 36 may be movable and configured to articulate coincident with the movable sections 35a, 35b of the patient support deck 34, if any. The mattress may be omitted in certain embodiments such that the patient rests directly on the patient support deck 34.

The base 26, intermediate support assembly 28, patient support deck 34, and mattress 36 each have a head end and a foot end corresponding to designated placement of the patient's head and feet, respectively, on the patient support apparatus 22. Referring to FIGS. 1, 2A and 2B, the patient support apparatus 22 comprises a longitudinal axis L along its length from the head end to the foot end, and a transverse axis T arranged perpendicularly to the longitudinal axis L.

The patient support apparatus 22 comprises a patient support surface 38 upon which the patient is supported. Any suitable structure of the patient support apparatus 22 may comprise at least a portion of the patient support surface 38 to support to the patient 24, either directly or indirectly. For example, the intermediate support assembly 28, the support frame 30, and/or patient support deck 34 may comprise the patient support surface 38. Often, an upper surface of the mattress 36 comprises the patient support surface 38. Additionally or alternatively, a separate, modular mattress pad adapted to be placed upon the mattress 36 may comprise the patient support surface 38. Support of the patient 24 could be effectuated in a number of different ways.

The patient support apparatus 22 may comprise side rails or panels 48 (see FIG. 1). The side rails or panels 48 may be coupled to the frame rails 40, 42, 44, 46, the patient support deck 34, or any other suitable structure on the patient support apparatus 22. The side rails or panels 48 may be movable between a raised position in which they block ingress and egress into and out of the patient support apparatus 22, one or more intermediate positions, and a lowered position in which they are not an obstacle to such ingress and egress. In the generally raised position, the side rails or panels 48 at least partially extend above the patient support surface 38 to prevent such ingress and egress. FIG. 1 shows side rails or panels 48 in a generally raised position on opposing sides of the patient support apparatus 22. In some cases, the side rails or panels 48 are fixed. In still other configurations, the patient support apparatus 22 may not comprise any side rails or panels 48.

Wheels 50 are coupled to the base 26 to facilitate transport over surfaces. The wheels 50 are arranged in each of four quadrants of the base 26 adjacent to corners of the base 26. In the embodiment shown in FIG. 1, the wheels 50 are caster wheels able to rotate and swivel during transport. Each of the wheels 50 forms part of a caster assembly 52 mounted to the base 26. It should be understood that various configurations of the caster assemblies 52 are contemplated. In some embodiments, the wheels 50 are not caster wheels. The wheels 50 may be non-steerable, steerable, non-powered, powered, or combinations thereof. Additional wheels are also contemplated, or conversely, the patient support apparatus 22 may not comprise any wheels.

As mentioned, the patient support apparatus 22 is configured to support and transport the patient 24 over surfaces. Along with other modes of transport contemplated, such as in an ambulance, transport of the patient 24 is associated with risk of inadvertent patient egress. During transport, the patient should remain situated on the patient support surface 38 to avoid injury, and preferably immobilized to receive uncompromised treatment from attending caregivers. To that end, the patient support system 20 comprises a harness assembly 54 configured to secure the patient 24 on the patient support surface 38 during transport. In a preferred embodiment, the harness assembly 54 secures the patient 24 proximate to the patient's shoulders and the hips, as illustrated in FIGS. 1, 2A and 2B.

The harness assembly 54 comprises one or more straps 56. The straps 56 may be elongated, flat fabric woven strips, commonly known as webbing. The straps 56 comprise mechanical characteristics, including tensile and breaking strengths, sufficient to restrain the patient 24 during transport, particularly in the event of increased or sudden impact forces (e.g., sharp turn or collision of a transport vehicle). The straps 56 may be formed of any suitable materials configured to secure the patient 24 during transport.

The straps 56 are positioned to secure the bilateral shoulders and bilateral hips of the patient 24. As such, the straps 56 may comprise one or more shoulder straps 57a configured to secure the shoulders of the patient 24 and one or more hip straps 57b configured to secure the hips of the patient 24 on the patient support surface 38. FIGS. 1 and 2A illustrate four straps arranged to create a crisscross configuration when viewed in plan, each with one end 58 coupled to the patient support apparatus 22 and another end 60 proximate to a junction 62 above the patient 24 positioned on the patient support surface 38. In a general sense, the junction 62 comprises an area representing an intersection of the harness assembly 54, such as the ends 60 of the shoulder straps 57a and the hip straps 57b. In another sense, the junction 62 may comprise a structural component of the harness assembly 54 to which one or more of the straps 56 are engaged. At least one of the ends 58, 60 of the straps 56 may be configured to removably couple to the patient support apparatus 22, the junction 62, and/or any suitable structure of the patient support system 20.

The junction 62 may be a unitary or multi-component structure having any one of a number of advantageous designs to be described. With reference to FIGS. 1 and 2A, the junction 64 may be disc-shaped and adapted to be coupled to the straps 56. For example, the straps 56 may each comprise a first coupler 59a (FIG. 8), which may be a buckle-type connection, configured to releasably couple with the junction 62. The first coupler 59a may alternatively be a hook-and-eye, keyway, bayonet or other connection. In another example, the straps 56 are fixedly coupled to the junction 62, such as through rivets, threading, and the like, with the straps 56 comprising the first coupler 59a configured to releasably couple with a coupler on the patient support apparatus 22. The coupling between the straps 56 and the junction 62 and/or the straps 56 and the patient support apparatus 22 preferably provides for relative pivoting so as to prevent kinking of the straps 56 and provide comfort for the patient with adjustability of the components of the tension adjustment system 68.

Figure 6:
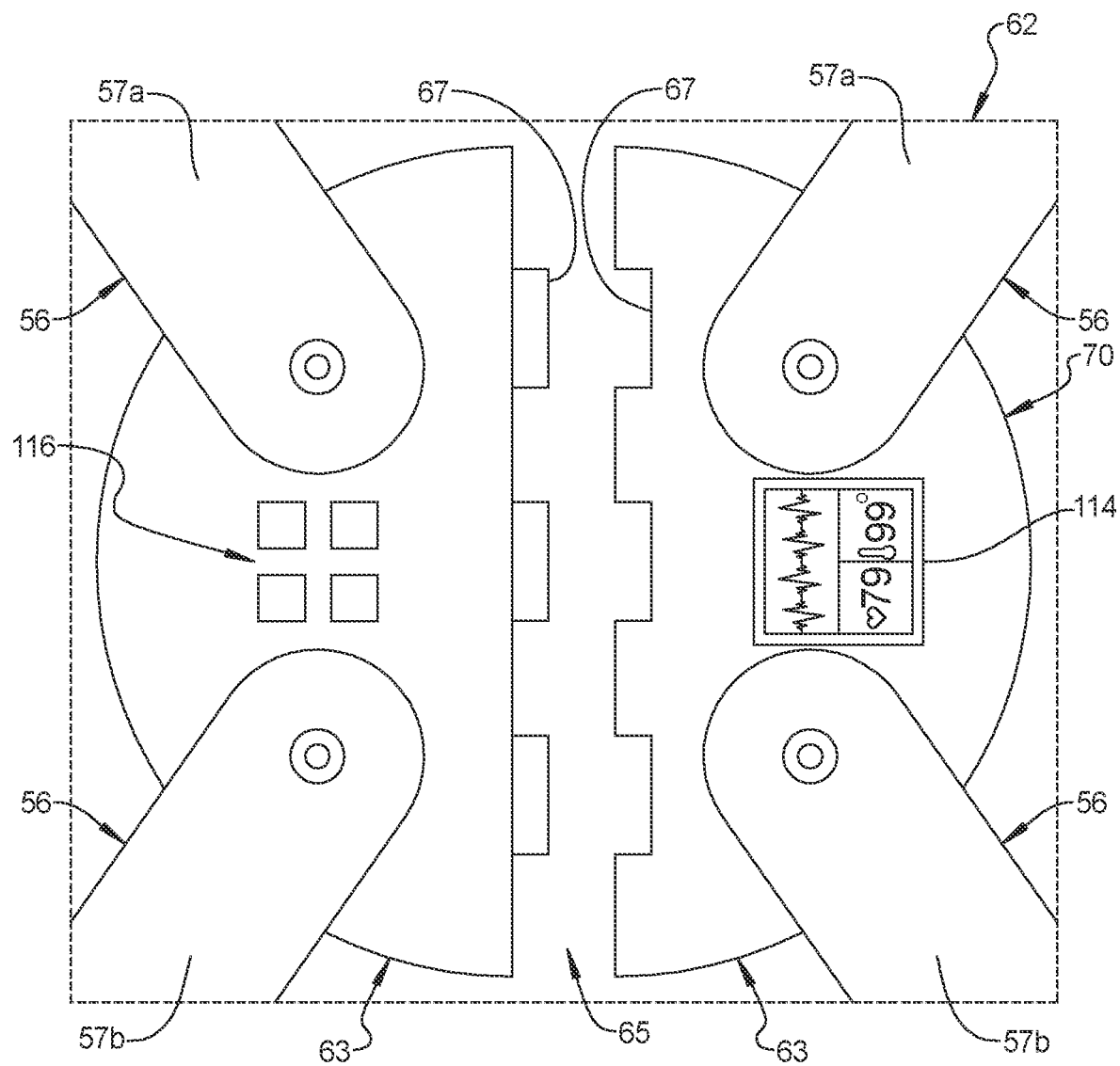
FIG. 6 is a plan view of one exemplary embodiment of the junction represented schematically in FIG. 2B.

FIG. 2B represents the junction 62 schematically with FIGS. 6 and 7 showing exemplary embodiments of the junction 62. The junction 62 of FIG. 6 comprises two portions 63, such as two split-halves, removably coupled to one another. Each of the portions 63 may be fixedly coupled to at least two of the straps 56 such that the straps 56 are not releasable from the portions 63. For example, FIG. 6 shows each of the portions 63 fixedly coupled to one of the shoulder straps 57a and one of the hip straps 57b to provide a generally V-shaped strap structure. Alternatively, one of the portions 63 may be fixedly coupled to the shoulder straps 57a, and the other one of the portions 63 may be fixedly coupled to the hip straps 57b, each to provide a generally V-shaped strap structure. The fixed connection shown permits relative pivoting between the straps 56 and the junction 62 to prevent kinking of the straps 56 and provide comfort for the patient with adjustability of the components of the tension adjustment system 68.

The two portions 63 may be quickly coupled and decoupled, such as at an interface 65 separating the two portions 63. Each of the portions 63 may comprise coupling features 67 adapted to be removably coupled. FIG. 6 shows tongues associated with one of the portions 63 with the tongues adapted to be received in grooves associated with the other one of the portions 63. The interface 65 may be provided by detents, latches, dovetail joints, and the like.

Figure 7A:
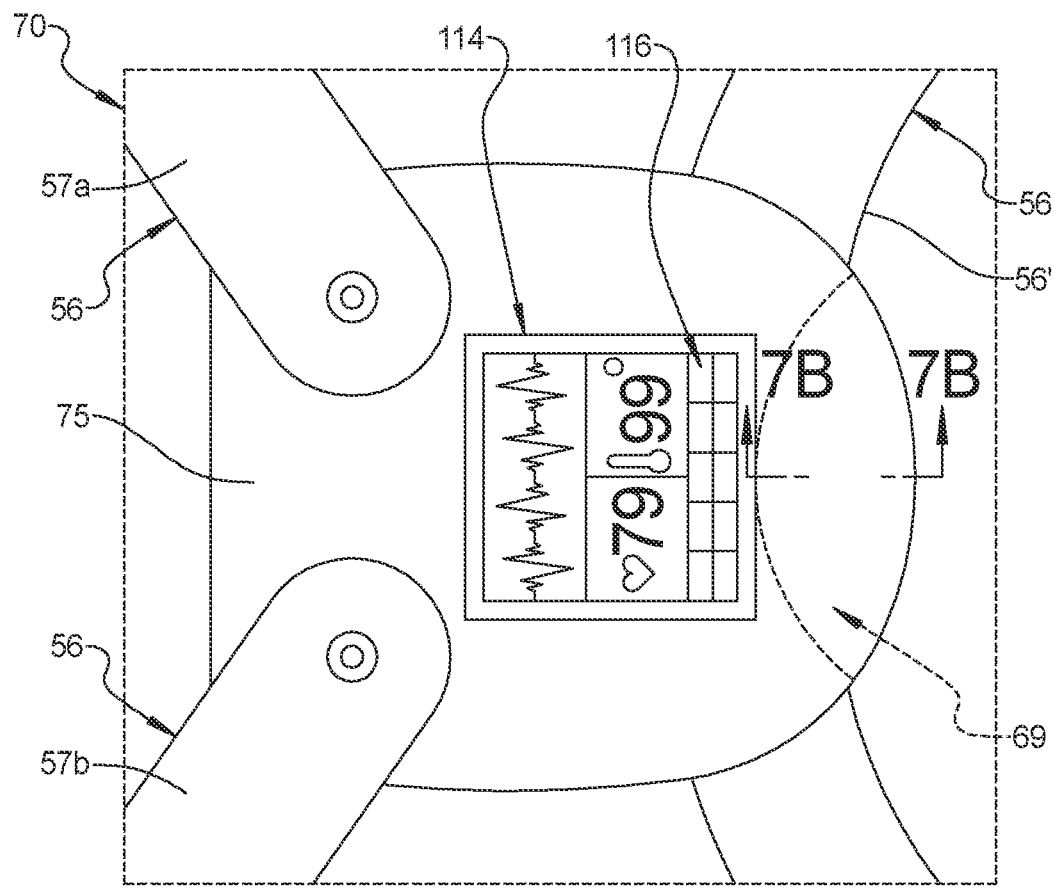
FIG. 7A is a plan view of another exemplary embodiment of the junction represented schematically in FIG. 2B.

Referring to FIG. 7A, the junction 62 may further comprise a retaining member 69 adapted to receive another one of the straps 56 of the harness assembly 54. The retaining member 69 may be positioned on the junction 62 opposite a fixed connection between the junction 62 and a shoulder strap 57a and a hip strap 57b. Strap 56 may comprise a continuous portion 56' that functions as both a shoulder strap 57a and a hip strap 57b. In other words, the shoulder strap 57a and the hip strap 57b may be integrated into a singular strap comprising the continuous portion 56'. The retaining member 69 may be adapted to receive the continuous portion 56'. The continuous portion 56' may be situated within the retaining member 69 such that, when the strap 56 is suitably tensioned by the tension adjustment system 68, the continuous portion 56' remains securely within the retaining member 69. When the tension of the strap 56 is decreased, the continuous portion 56' may be quickly decoupled from the junction 62.

Figure 7B:
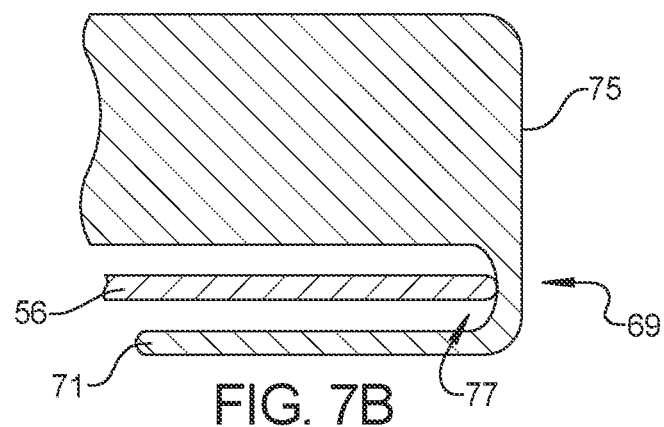
FIG. 7B is a cross-sectional view of the junction of FIG. 7A taken along lines 7B-7B.

In the illustrative embodiment of FIGS. 7A and 7B, the retaining member 69 comprises a lip 71 that is generally U-shaped or V-shaped when viewed in elevation. The lip 71 may be extend downwardly (i.e., towards the patient 24) or upwardly (i.e., away from the patient 24) from a main body 75 of the junction 62. The lip 71 may extend along a portion or an entirety of a width of the main body 75. The lip 71 may be unitarily formed or fixedly coupled to the main body 75. The continuous portion 56' may be received within a channel 77 defined between the lip 71 and the main body 75.

With the junction 62 shown in FIGS. 7A and 7B, it may be necessary to make only one connection to secure the patient 24 to the patient support apparatus 22. More specifically, after the patient 24 is positioned on the patient support surface 38, the desired position of the junction 62 is approximated, and the continuous portion 56' of the strap 56 is positioned with the channel 77 of the receiving member 69, such as by looping it around the lip 71. The tension of the strap 56 is adjusted, by the tension adjustment system 68 or otherwise, such that the continuous portion 56' may not extend around the lip 71 to inadvertently decouple from the junction 62. Further, the continuous portion 56' of the strap 56 is movable within the channel 77 of the receiving member 69. For example, the sliding of the continuous portion 56' within the channel 77 assists with positioning a patient interface 70 in a manner to be described.

The present disclosure further contemplates that a greater or fewer number of straps 56 may be utilized. For example, the shoulder straps 57a may comprise a singular V-shaped strap that removably couples with a singular V-shaped strap comprised of the hip straps 57b. For another example, one of the shoulder straps 57a and one of the hip straps 57b may comprise a singular V-shaped strap that removably couples with a singular, counterposing V-shaped strap from the opposing side of the patient support apparatus 22. Still yet further, a groin strap 59c (FIG. 14) may be provided.

An advantage of the harness assembly 54 is to provide chest compressions to the patient 24 while the patient 24 is secured to the patient support surface 38. Doing so can at least partially automate the resource-intensive task of cardiopulmonary resuscitation (CPR) during transport, often to the emergency department, thereby permitting first responders to provide additional medical services to the patient 24. Consequently, the patient support system 20 comprises a chest compression system 80 configured to provide chest compressions to the patient 24 while the patient 24 is secured to the patient support surface 38 with the harness assembly 54.

According to the American Heart Association, optimal CPR requires depressing the human chest one and one half to two inches, which can equate to 100 to 125 pounds of force. To provide satisfactory chest compressions while the patient 24 is secured to the patient support surface 38 with the harness assembly 54, the chest compression system 80 is advantageously integrated into the harness assembly 54. More particularly, in one embodiment, the chest compression system 80 comprises a tension adjustment system 68 (see FIG. 5) and the patient interface 70 operably coupled to the harness assembly 54. The tension adjustment system 68 is configured to selectively adjust the tension of the harness assembly 54 in a manner that provides compressions to the patient 24. More specifically, the tension adjustment system 68 comprises one or more actuators 72 configured to selectively adjust the tension of the straps 56 of the harness assembly 54.

Referring to FIGS. 2A and 2B, the actuators 72 are coupled to the patient support apparatus 22. The actuators 72 may be coupled to the intermediate support assembly 28, the support frame 30, the patient support deck 34, and/or any other suitable structure on the patient support apparatus 22. In the exemplary embodiment of FIGS. 2 and 3, the actuators 72 are coupled to the frame rails 40, 42, 44, 46 of the support frame 30. The actuators 72 may comprise shoulder strap actuators 73a and hip strap actuators 73b. In the illustrated embodiment, each of the shoulder strap actuators 73a are coupled to the third frame rail 44, and the hip strap actuators 73b are coupled to each of the first frame rail 40 and the second frame rail 42. The present disclosure contemplates each of the actuators 72 may be coupled to any one or more of the frame rails 40, 42, 44, 46 or any other suitable portion of the patient support apparatus 22.

Further, while the illustrated embodiment comprises two of each of the shoulder strap actuators 73a and hip strap actuators 73b, any number of actuators may be provided. For example, the hip strap actuators 73b may be replaced with the second couplers 59b (FIG. 13) of the patient support apparatus 22 (e.g., portion of buckle-type connection), or the hip straps 57b may be otherwise fixedly secured to the patient support apparatus 22 such that the tension of the hip straps 57b may not be selectively adjusted. In such an example, the tension of the harness assembly 54 is controlled with the shoulder strap actuators 73a alone.

The tension adjustment system 68 is positioned such that the harness assembly 54 secures the bilateral shoulders and hips of the patient 24 to the patient support surface 38. Because the straps 56 of the harness assembly 54 generally intersect at the junction 62, the actuators 72 of the tension adjustment system 68 may be coupled to the patient support apparatus 22 along the head end, foot end, and opposing sides in any suitable manner such that the straps 56 are positioned adjacent the shoulders and hips of the patient 24. With continued reference to FIG. 2A, the shoulder strap actuators 73a are coupled at the head end proximate to opposing sides of the patient support apparatus 22. More specifically, one of the shoulder strap actuators 73a are coupled proximate an intersection between the first frame rail 40 and the third frame rail 44, and another one of the shoulder strap actuators 73a is coupled proximate an intersection between the second frame rail 42 and the third frame rail 44. The hip strap actuators 73b are coupled along opposing sides of the patient support apparatus 22. More specifically, one of the hip strap actuators 73b is coupled to each of the first frame rail 40 and the second frame rail 42 at approximately thigh-level of the patient 24, or approximately one-third upwardly from the foot end of the patient support apparatus 22.

The position of the actuators 72 of the tension adjustment system 68 may be adjustable. For example, the actuators 72 may be removably coupled to the frame rails 40, 42, 44, 46 or other suitable structure such that the actuators 72 may be decoupled, moved, and recoupled in a desired position. For another example, the actuators 72 may be slidably coupled to the frame rails 40, 42, 44, 46 or other suitable structure. In such an example, the frame rails 40, 42, 44, 46 may comprise slots within which a key-like protrusion associated with the actuators 72 may be slidably disposed, and/or the actuators 72 may comprise a throughbore which slidably engages the frame rails 40, 42, 44, 46. The straps 56 may be pivotally coupled to the actuators 72 (and/or the actuators 72 pivotally coupled to the frame rails 40, 42, 44, 46) so as to prevent kinking of the straps 56 and provide comfort for the patient 24 regardless of the position of actuators 72 along the frame rails 40, 42, 44, 46. The removability of the tension adjustment system 68 advantageously permits the harness assembly 54 and the chest compression system 80 to be retrofit on existing patient support apparatuses, and the adjustability of the tension adjustment system 68 provides for patient comfort while satisfactorily securing the patient 24 to the patient support surface 38.

Figure 8:
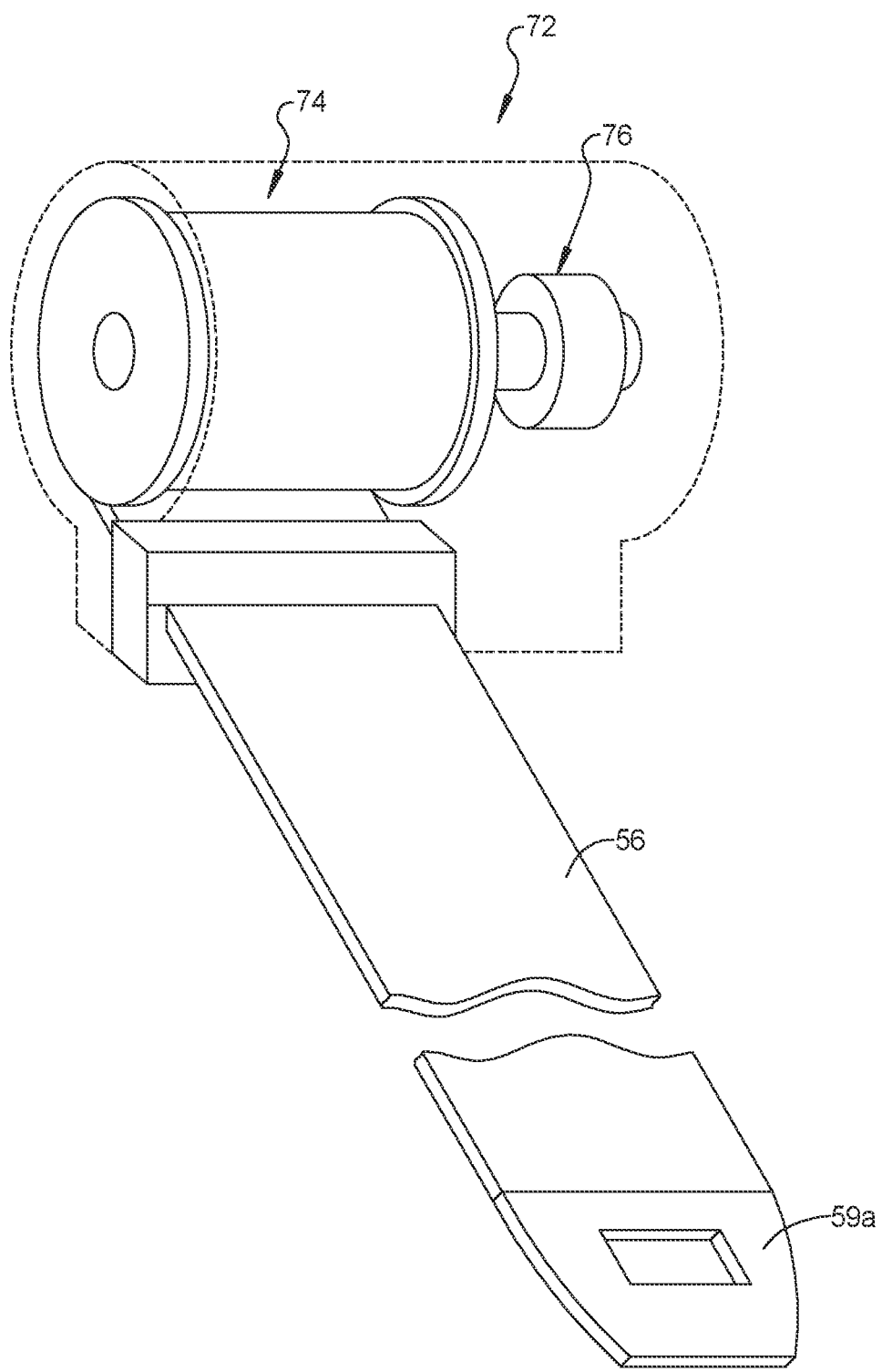
FIG. 8 is a schematic illustration of an actuator of a tension adjustment system.

The tension adjustment system 68 comprises the actuators 72 configured to selectively adjust the tension of the straps 56 of the harness assembly 54. In certain embodiments, such as depicted in FIG. 2A, tension of each of the straps 56 is selectively adjusted with one of the actuators 72 of the tension adjustment system 68. Each of the straps 56 comprises the first coupler 59a adapted to be removably coupled to the junction 64 or a suitable structure of the patient support apparatus 22, such as the frame rails 40, 42, 44, 46. FIG. 8 shows the first coupler 59a comprises a buckle-type connection.

FIGS. 9A-9C and 10 show the first coupler 59a comprises a spherical coupler adapted to be received by a coupling device 172. The coupling device 172 of FIGS. 9A-9C and 10 provide for a removable connection with the spherical coupler while providing movement of the straps 56 relative to the coupling device 172 in at least two degrees of freedom. The coupling device 172 comprises a housing 174 adapted to be mounted to a suitable structure of the patient support apparatus 22, such as the frame rails 40, 42, 44, 46. Additionally or alternatively, the housing 174 may be functionally integrated with the junction 62.

Figure 9A:
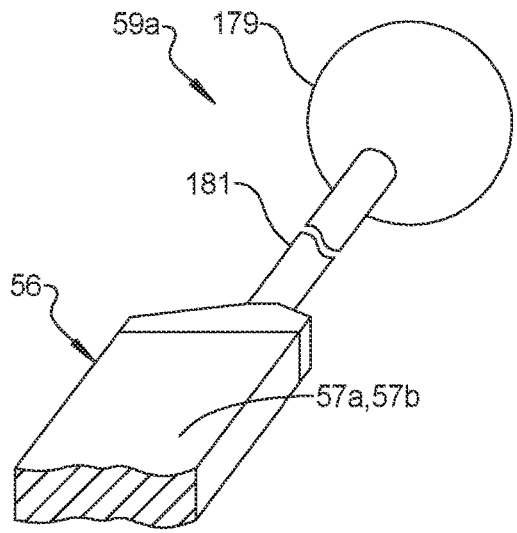
FIG. 9A is a perspective view of a coupler in accordance with an exemplary embodiment of the present disclosure.
Figure 9B:
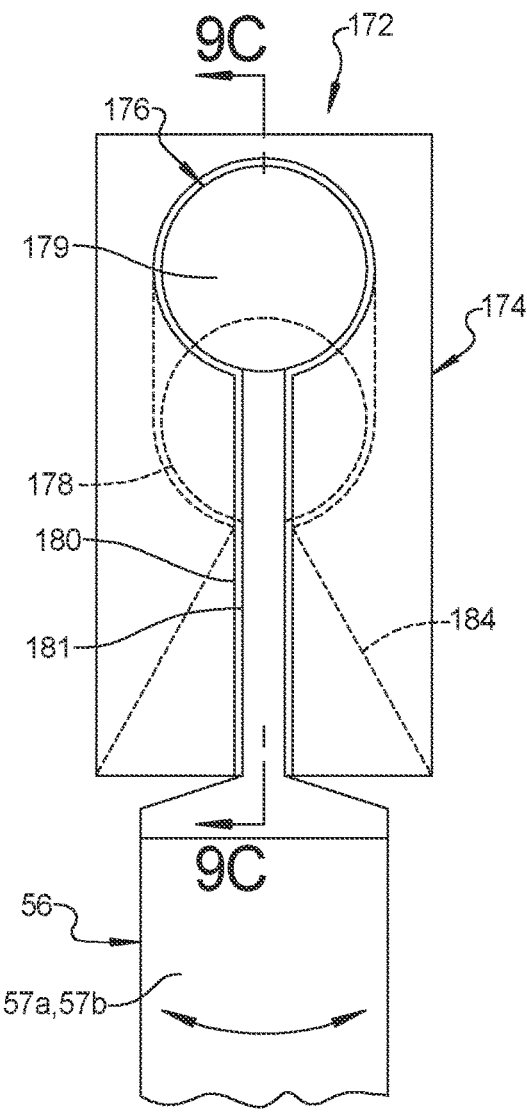
FIG. 9B is a top plan view of the coupler of FIG. 9A inserted into a coupling device.
Figure 9C:
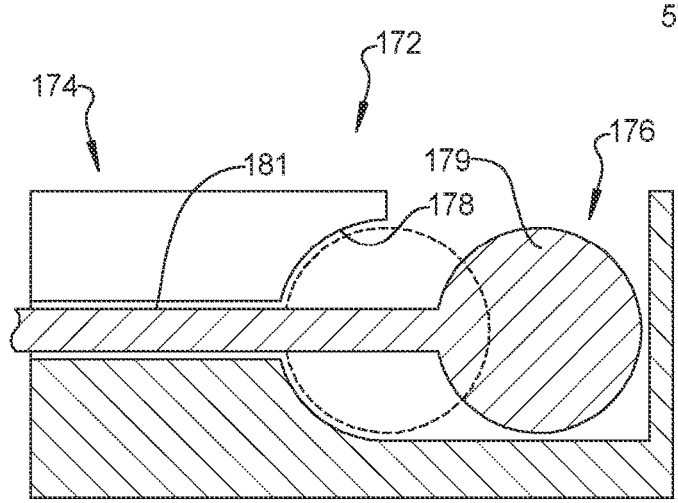
FIG. 9C is a cross-sectional view of the coupler and coupling device of FIG. 9B taken along lines 9C-9C.

Referring to FIGS. 9A-9C, the coupling device 172 comprises a cavity 176 within the housing 174 with the cavity 176 adapted to receive the first coupler 59a. The cavity 176 may comprise a socket 178 defining at least a portion of a sphere, and a slotted portion 180. The socket 178 and the slotted portion 180 are generally shaped to the characteristics of the first coupler 59a while being slightly larger so as to receive the first coupler 59a therein. The first coupler 59a may be positioned above the coupling device 172 in alignment with the cavity 176 and the slotted portion 180. The first coupler 59a is lowered into the coupling device 172 with the spherical coupler 179 positioned within the cavity 176 and a shaft 181 of the first coupler 59a extending through the slotted portion 180. Tension may be provided to the strap 56 such that the first coupler 59a and the coupling device 172 remain engaged by virtue of the spherical coupler 179 being pulled into engagement with the socket 178 (note that FIGS. 9B and 9C illustrate the insertion of the spherical coupler 179 into the coupling device 172 and hidden lines represent a position of the spherical coupler 179 after tension pulls the spherical coupler 179 into the socket 178).

The first coupler 59a is adapted to be pivotable within the coupling device 172. The housing 174 may define a triangular void 184 adapted to permit movement of the shaft 181 of first coupler 59a. Further, movement of the first coupler 59a relative to the coupling device 172 may be provided in one, two, or three or more degrees of freedom based on the spherical coupler 179 within the socket 178 and the triangular void 184.

Figure 10:
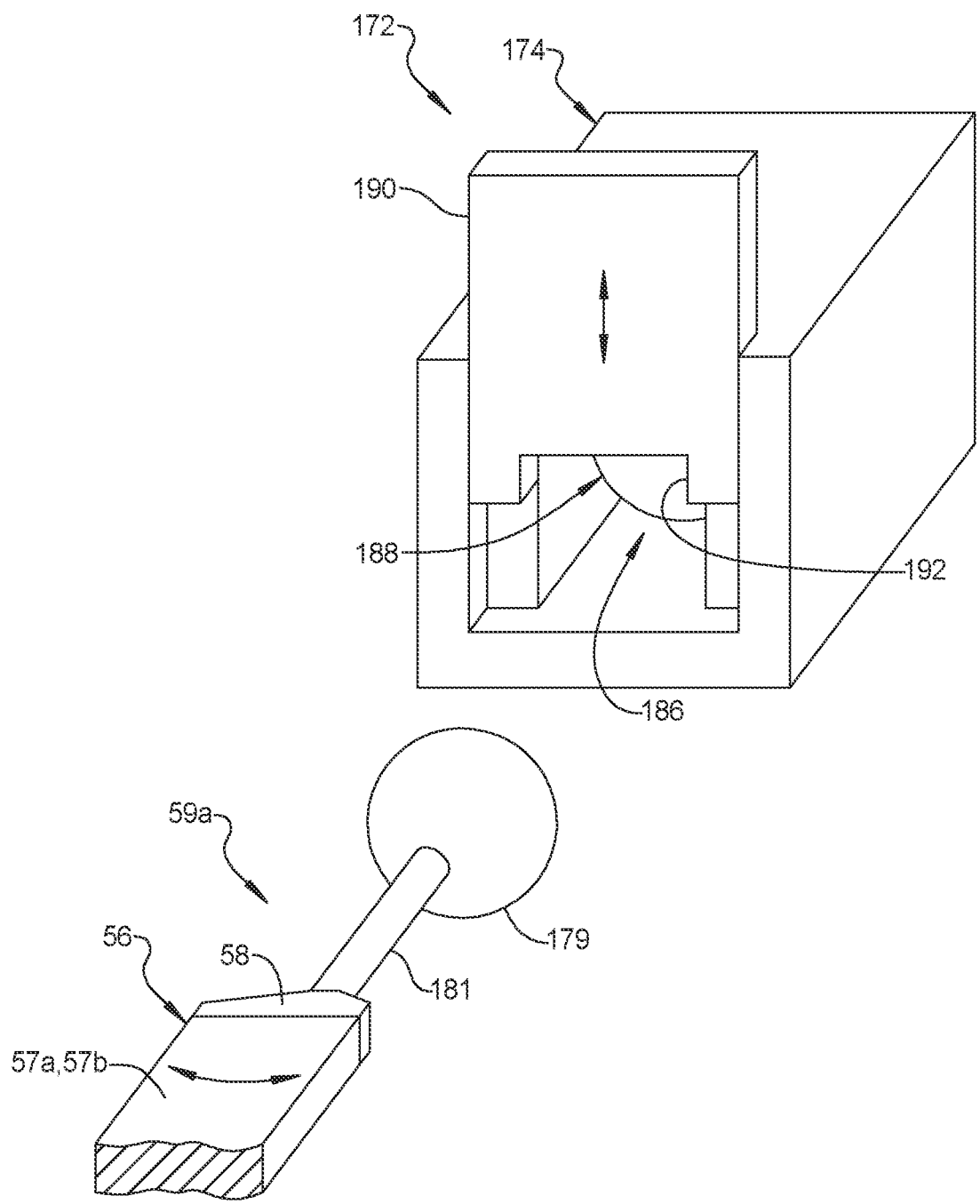
FIG. 10 is a perspective view of a coupler system in accordance with another exemplary embodiment of the present disclosure.

Referring to FIG. 10, the housing 174 of FIG. 10 comprises a cavity 186 adapted to receive the first coupler 59a. The cavity 186 may be associated with a socket 188 defining at least a portion of a sphere. The socket 188 is adapted to receive the spherical coupler 179 of the first coupler 59a with at least a portion of the shaft 181 of the first coupler 59a received within the cavity 186. The housing 174 further comprises a barrier 190 movable from a first position to a second position. The barrier 190 may be slidable between the first position in which an opening is suitably sized for insertion of the first coupler 59a into the cavity 186, and a second position with no such opening. In the second position the barrier 190 may provide a slot 192 through which the shaft 181 of the first coupler 59a extends with the size of the slot 192 providing an interference fit with the spherical coupler 179.

The spherical coupler 179 is positioned within the socket 188 of the cavity 186 with the barrier 190 in the first position. The barrier 190 is moved from the first position to the second position to provide the slot 192 for the shaft 181 and the interference fit with the spherical coupler 179.

The first coupler 59a is adapted to be pivotable within the cavity 186 of the coupling device 172 (as shown by the arrows in FIG. 10). The cavity 186 proximate the shaft 181 provides suitable clearance to permit movement of the shaft 181 within the cavity 186. Further, movement of the first coupler 59a relative to the coupling device 172 may be provided in one, two, or three or more degrees of freedom based on the spherical coupler 179 within the socket 188 and the clearance within the cavity 186.

Referring to FIG. 2B, the harness assembly 54 may further comprise leg strap 55 for providing supplemental restraint to the patient 24. FIG. 2B shows the leg strap 55 generally positioned across the legs of the patient 24. The leg strap 55 may be coupled to any suitable structure of the patient support apparatus 22 such as the frame rails 40, 42, 44, 46. The leg strap 55 may be operably coupled to one or more of the actuators 72 of the tension adjustment system 68 to selectively adjust the tension of the leg strap 55. The leg strap 55 may be movable along the frame rails 40, 42, 44, 46. For example, the actuators 72 coupled to the frame rails 40, 42 may be slidable so as to move the leg strap 55 along the longitudinal axis L. Once in a desired position along the legs of the patient 24, the actuators 72 may be locked to prevent further movement and position the leg strap 55.

As mentioned, the chest compression system 80 comprises the patient interface 70. The patient interface 70 of the chest compression system 80 comprises one or more systems and devices configured to effectuate depressing the chest of the patient 24. The tension adjustment system 68 is configured to adjust the tension of one or more of the straps 56 of the harness assembly 54 in a manner that causes the patient interface 70 to forcefully depress the chest of the patient 24. To that end, the tension adjustment system 68 comprises one or more tension elements 74 (also referred to as pulling elements) coupled to the one or more straps 56. Referring again to FIG. 8, an exemplary actuator 72 is illustrated. The tension element 74 may comprise a rotor or winding device secured to an end of the strap 56 and operably coupled to a motor 76. The actuator 72, and more particularly the motor 76, winds the tension element 74 to adjust the tension of the strap 56.

Figure 3:
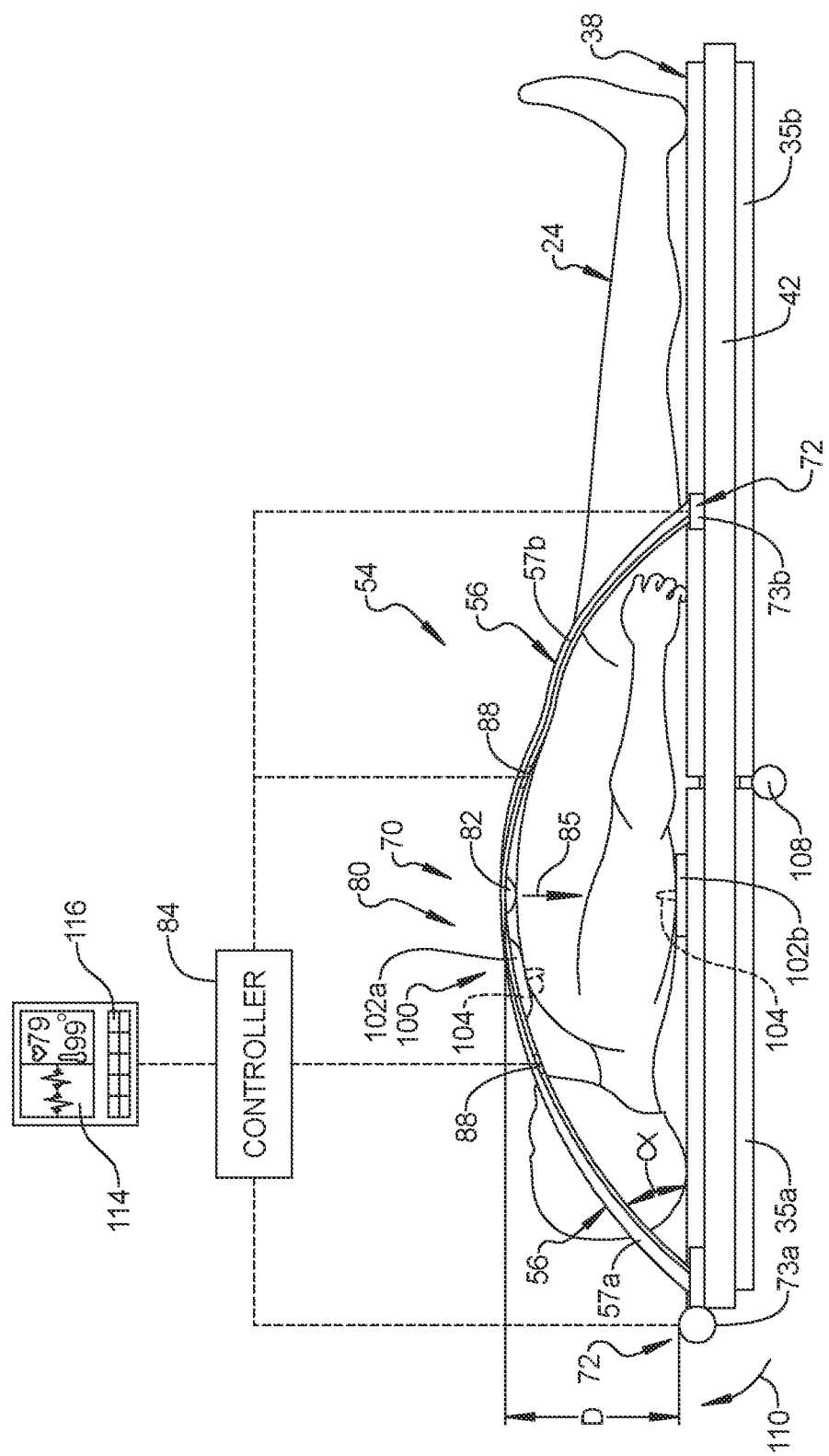
FIG. 3 is an elevational view of the patient support system of FIG. 1.

Referring to FIG. 3, the patient interface 70 in accordance with one exemplary embodiment comprises one or more projections 82 coupled to the harness assembly 54. The projection 82 may be coupled to one or more of the straps 56 and/or the junction 62, and may be positioned above the patient's lower sternum and/or at the optimal placement for performing CPR compressions. The projection 82 is comprised of semi-rigid or rigid material so as to suitably transfer forces to the patient 24 from the harness assembly 54 as the tension is adjusted during operation. Exemplary suitable materials may comprise plastic, metal, composite, or combinations thereof.

Figure 5:
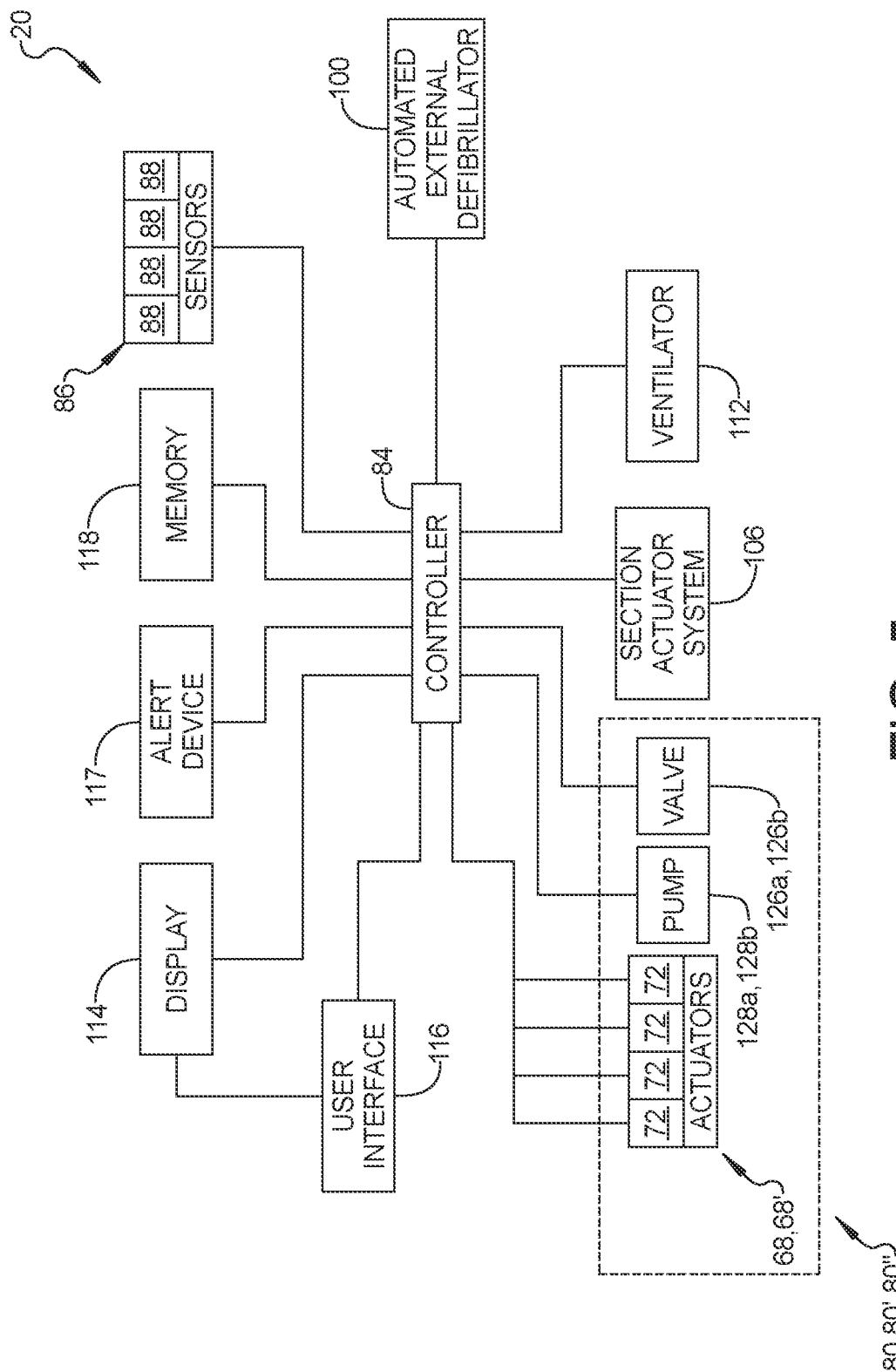
FIG. 5 is a schematic diagram of a control system.

Referring to FIG. 5, the patient support system 20 further comprises a controller 84 in communication with the chest compression system 80 and configured to control operation of the chest compression system 80. The controller 84 is in electronic communication with and configured to control numerous electromechanical and electronic components of the patient support system 20 as disclosed throughout the present disclosure. The controller 84 is in electronic communication with the tension adjustment system 68 of the chest compression system 80. More specifically, the controller 84 is configured to control the actuators 72 of the tension adjustment system 68 to selectively adjust the tension of the harness assembly 54.

The patient support system 20 still further comprises a sensor system 86 in communication with the controller 84 such that the controller 84 is configured to control the operation of the chest compression system 80 based on signals received from the sensor system 86. The sensor system 86 comprises one or more sensors 88. The sensors 88 are integrated into the harness assembly 54 such that the sensors 88 may be coupled to the straps 56. In the exemplary embodiments illustrated in FIGS. 2A and 2B, one of the sensors 88 is coupled to each of the shoulder straps 57a and the hip straps 57b. However, it should be appreciated that the sensors 88 may be removably coupled, installed, or otherwise retrofitted with the harness assembly 54 in any suitable manner. Further, the sensors 88 may be associated with the leg strap 55 and may be in communication with the sensor system 86. For example, the sensors 88 may be load cells or strain gauges operably coupled to the leg strap 55 such that, in conjunction with the tension adjustment system 68, the leg strap 55 is automatically placed in the appropriate tension.

At least some of the sensors 88 are positioned proximate the patient's chest to obtain accurate physiologic data related to cardiopulmonary functioning of the patient 24. The sensors 88 or additional sensors may be coupled to any suitable structure of the harness assembly 54 and/or the patient support apparatus 22. The sensor system 86 and/or the controller 84 may be wired or wirelessly integrated with its operating environment. For example, the sensor system 86 and/or the controller 84 may be configured to wirelessly send and receive data from an ambulance, hospital room, and the like, having similar capabilities. The wireless connection may be effected through Wi-Fi, Bluetooth®, Zig-Bee®, infrared (IR), and the like, to transmit data between the controller 84, the sensor system 86, and the operating environment.

The sensor system 86 is configured to measure, determine, detect, or otherwise gather any number and type of data, including but not limited to physiologic, environmental, spatial, and movement data. The sensor system 86 may comprise one or more of a respiration sensor, an oxygen sensor, a carbon dioxide sensor, a temperature sensor, a heart rate sensor, a force sensor, a load cell, a strain gauge, a pressure sensor, a near-infrared spectrometer, an accelerometer, a gyroscope, a pulse oximeter, an electrocardiogram sensor, or a piezoelectric sensor. For example, the harness assembly 54 may comprise accelerometers and/or gyroscopes configured to monitor movement of the harness assembly 54. The accelerometers and/or the gyroscopes may track certain dynamics of patient movement during transport, and directly or indirectly track associated vehicle dynamics should the patient 24 be transported in an ambulance. The sensor system 86 may provide vehicle data to the controller 84. In another example, the accelerometers and/or the gyroscopes may detect a sudden change in relative movement of the harness assembly 54 or the vehicle (e.g., a collision of an ambulance), and provide an accident signal to the controller 84. In response to the accident signal received from the sensor system 86, the controller 84 may perform any number of responsive measures, including, but not limited to, controlling the tension adjustment system 68 to ensure the patient 24 is adequately secured to the patient support surface 38. For another example, the sensor system 86 may comprise near-infrared spectroscopy configured to measure blood flow and related characteristics. One such exemplary vascular monitoring system and sensor is disclosed in U.S. Patent Application Publication No. 2015/0327777 filed May 11, 2015, by inventors Marko Kostic et al. and entitled TISSUE MONITORING APPARATUS AND SYSTEM, which is hereby incorporated by reference herein in its entirety. The functionality of the sensor system 86 is disclosed throughout the present disclosure.

In addition to the controller 84, sensor system 86, and other electronic components disclosed herein, the patient support system 20 may comprise signal acquisition and processing circuitry, embedded software and algorithms, and the like, to carry out the functions described herein.

An exemplary operation of the chest compression system 80 will now be described with reference to FIG. 3. The sensors 88 may detect a cardiac event, and more specifically, an electrocardiographic or heart rate sensor may detect physiologic changes requiring acute intervention. The sensor system 86 provides an event signal to the controller 84. In response to the event signal received from the sensor system 86, the controller 84 controls the actuators 72 to wind the tension elements 74 to adjust the tension of the straps 56. The actuators 72 are positioned on, at, or below the patient support surface 38, whereas the projection 82 coupled to the harness assembly 54 is positioned in an abutting relationship with the chest of the patient 24 above the patient support surface 38. The difference in vertical position between the tension element 74 of each actuator 72 and the projection 82 is a distance D such that, as the actuators 72 wind the tension elements 74, the increase in tension of the straps 56 has a force component that urges the projection 82 towards the patient 24 in the direction of arrow 85. The force component in the direction of arrow 85 is approximately the product of the tension force and the sine of an angle α defined between the directions of the straps 56 proximate the tension element 74 and horizontal. The projection 82 is urged in the direction of arrow 85 to depress the chest of the patient 24 with the optimal force to achieve maximum results from the CPR compression. The force with which the projection 82 depresses the chest of the patient 24 is a function of the increase in tension of the harness assembly 54, which may be measured by the sensor system 86 comprising a force sensor, a load cell, a strain gauge, an accelerometer, and/or a gyroscope, among others. For example, strain gauges may be coupled with the straps 56 to measure material strain, from which tension of the straps 56 is determined. The sensor system 86 provides a force signal to the controller 84 such that the tension can be adjusted in real-time as a continuous feedback loop. Based on the force signal and/or other signals from the sensor system 86, the controller is configured to control the one or more actuators 72.

As commonly known, chest compressions are relatively quick and repetitive in nature. Once the desired CPR compression is achieved, the controller 84 provides a signal to the actuators 72 to decrease the tension of the harness assembly 54, and more particularly the straps 56. Essentially, the motor 76 of the actuator 72 is operated in a direction to unwind the tension element 74. The compression on the patient's chest from the projection 82 is eased. The selective increase and decrease in tension of the harness assembly 54 results in a compression rate that may be adjusted as desired. For example and in accordance with typical recommended CPR protocol, the compression rate is at least 100 compressions per minute or any other rate determined to be suitable to provide treatment. The compression rate may be detected by the sensor system 86 and a rate output signal provided to the controller 84 in real-time as a continuous feedback loop. Based on the rate output signal received by the controller 84, the controller 84 may adjust the actuators 72 accordingly to increase and decrease the tension of the harness assembly 54 in a predetermined or customizable manner.

In one embodiment previously disclosed, the actuators 72 comprise the shoulder strap actuators 73a and the hip strap actuators 73b. The controller 84 may be configured to independently control each of the shoulder strap actuators 73a and the hip strap actuators 73b such that the precise magnitude and direction of the force from the patient interface 70 is applied to the chest of the patient 24. For example, if the desired direction of the applied force from the projection 82 is slightly angled towards the patient's head, the controller 84 may control the shoulder strap actuators 73a to increase the tension more rapidly relative to the hip strap actuators 73b. In such an example, the harness assembly 54 is influenced to translate towards the head end of the patient support surface 38. Whereas simultaneous tensioning typically results in a vertical force, the result of the present example is a longitudinal horizontal force component (i.e., along axis L) of the projection against the patient 24 secured to the patient support surface 38. Similarly, each of the shoulder strap actuators 73a or each of the hip strap actuators 73b may be independently controlled to generate a horizontal force component (i.e., along axis T). Independent control of each of the shoulder strap actuators 73a and the hip strap actuators 73b may be advantageous based on body habitus, refinements in CPR protocol, and/or other circumstances requiring applied horizontal forces or the like.

Another advantage of selectively controlling and adjusting the tension of the harness assembly 54 is to ensure proper positioning of the patient interface 70 against the patient 24. As noted, CPR protocol recommends compression of the patient's lower sternum. More particularly, when using one's hands, CPR protocol recommends placing one's palms two finger-widths above the lowermost part of the sternum. Ensuring proper positioning of the patient interface 70 maximizes the efficacy of the CPR compressions. The patient interface 70 may be movable relative to the patient 24 to be properly located with respect to the patient 24 while the chest compression system 80 provides chest compressions to the patient 24.

Figure 4A:
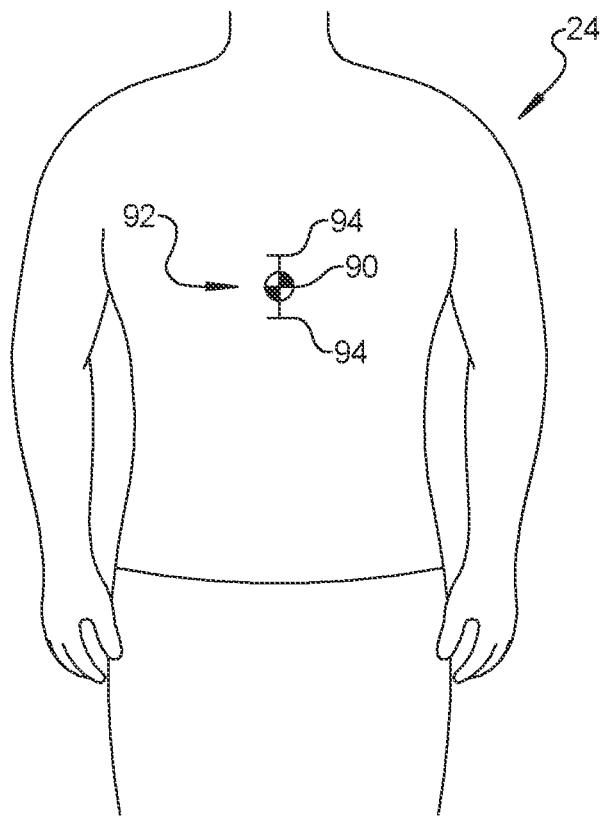
FIG. 4A is a top plan view of a human torso with superimposed positional indicators.

Referring now to FIG. 4A, a schematic illustration of a portion of the patient 24 is shown with an optimal compression location 90. The optimal compression location 90 may be approximately two finger-widths above the lowermost part of the sternum according to CPR protocol or other suitable locations for performing CPR compressions. Based on the lack of visualization of internal anatomy as well as the emergent nature of the medical situation, inherent variance is expected. A suitable compression location 92 comprises a predefined tolerance 94 of the optimal compression location 90. The controller 84 is configured to control the tension adjustment system 68 to move and/or position the patient interface 70 within the suitable compression location 92.

Figure 4B:
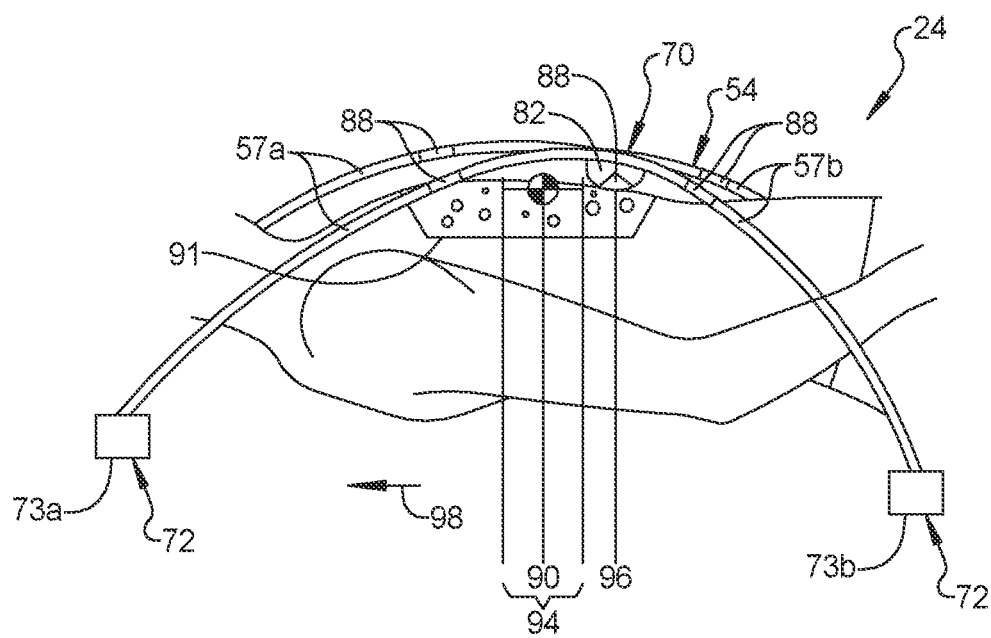
FIG. 4B is an elevational view of the human torso and the positional indicators of FIG. 4A, with a schematic illustration of the harness assembly and the chest compression system in accordance with exemplary embodiments of the present disclosure.

With concurrent reference to FIG. 4B, the sensor system 86 may be configured to determine a current position 96 of the patient interface 70. In the exemplary embodiment of FIGS. 4A and 4B, a sensor 88 may be positioned within the projection 82 and communicating with the controller 84 to determine the current position 96 of the projection 82. For example, the optimal compressional location 90 may be printed as a unique optical pattern on a positioning guide 91 attached to the patient 24 by the attending caregiver. The exemplary positioning device 91 of FIG. 4B comprises a sticker or drape positioned across the chest of the patient 24. The sensor 88 disposed in the projection 82 may comprise an optical sensor (e.g., charge-coupled device (CCD) complementary metal-oxide semiconductor (CMOS), etc.) configured to detect the unique optical pattern associated with the optimal compression location 90 via pattern recognition techniques. Additional printed patterns may surround the optimal compression location 90 and be sensed to determine the locations of the sensor 88 in the projection 82 relative to the optimal compression location 90 so that the location of the projection 82 relative to the optimal compression location 90 is known. An additional sensor (not shown) may be coupled to the harness assembly 54 and/or the patient interface 70 in such a manner to detect the unique optical pattern associated with the optimal compressional location 90.

Prior to or upon being secured to the patient support surface 38 with the harness assembly 54, an attending caregiver attaches the sticker or other similar device comprising the unique optical pattern to the patient. The sensor 88 in the projection 82 detects the printed patterns to determine the location of the projection 82 relative to the optimal compression location 90. Based on the feedback from the sensor 88 in FIG. 4B, the sensor system 86 and/or the controller 84 determine the current position 96 of the patient interface 70 relative to the optimal compression location 90. The controller 84 controls the tension adjustment system 68 to move and/or position the patient interface 70 based on the relative locations of the projection 82 until the projection 82 is within the suitable compression location 92.

Other exemplary sensors 88 to facilitate moving and/or positioning the patient interface 70 within the suitable compression location 92 may comprise infrared, ultrasonic, fluoroscopic, or x-ray imaging devices configured, in combination with the controller 84 and a display 114 (FIGS. 3, 7 and 8), to display the bony anatomy of the patient 24. In still yet another example, the operating environment such as the ambulance may be equipped with imaging device(s) (e.g., camera) configured to acquire one or more images of the harness assembly 54 positioned over the patient 24. The image data is transmitted to the controller 84, wirelessly or otherwise, and the controller 84 determines whether the patient interface 70 is within the suitable compression location 92. Other methods for determining the current position 96 of the patient interface 70 are contemplated.

FIG. 4B shows the current position 96 is not within the predefined tolerance 94 of the optimal position 90. The sensor system 86 transmits a positioning signal to the controller 84. In response to the positioning signal received from the sensor system 86, the controller 84 controls the tension adjustment system 68 to move the patient interface 70 within the suitable compression location 92. In the present example, the controller 84 controls the shoulder strap actuators 73a to increase the tension of the shoulder straps 57a while simultaneously controlling the hip strap actuators 73b to decrease the tension (i.e., release) the hip straps 57b. The result is a horizontal force component in the direction of arrow 98 that translates the harness assembly 54 towards the head end of the patient support apparatus 22. The sensor system 86 continuously monitors the current position 96 of the projection 82 and updates the controller 84 in a continuous feedback loop. Once the current position 96 of the projection 82 is within the predefined tolerance 94 of the optimal location 90, the controller 84 terminates the operation of the actuators 72, and adjusts the harness assembly 54 to the desired tension. In some cases, attending caregivers may be able to adjust the current position 96 of the patient interface 70 by controlling one or more of the actuators 72 either locally on each actuator 72 or through a user interface 116 (FIGS. 3, 5, 7 and 8) described further below. The patient interface 70 is maintained within the predefined tolerance 94 of the optimal location 90 throughout the process of administering the chest compressions to compensate for any movement of the patient 24 supported on the mattress 36.

In certain embodiments, the sensor system 86 may be adapted to detect the position of the strap housings (e.g., the actuators 72) about the frame rails 40, 42, 44, 46 to measure the location of the patient 24 on the patient support surface 33. Based on the position of the patient 24, the controller 84 is adapted to determine optimal compression location 90 of the patient interface 70 and the manner to position the patient interface 70 in the optimal compression location 90 by controlling one or more of the actuators 72. For example, subsequent to the harness assembly 54 being suitably connected, the sensor system 86 may be adapted to automatically detect and position the patient interface 70 in the optimal compression location 90 (i.e., connect and configure). Alternatively, the optimal compression location 90 may be determined or programmed in advance of the harness assembly 54 being connected, and subsequent to the harness assembly 54 being connected, the sensor system 86 may be adapted to automatically position the patient interface 70 in the predetermined or preprogrammed optimal compression location 90 (i.e., configure and connect).

Further systems and devices may also be provided to improve patient care while the patient 24 is secured to the patient support surface 38 of the patient support apparatus 22. The patient support system 20 may comprise an automated external defibrillator (AED) 100 integrated into the harness assembly 54. An AED is a device that automatically treats cardiac arrhythmias through defibrillation—the application of electrical therapy—to allow the heart to reestablish an effective rhythm.

The AED 100 comprises defibrillator electrodes 102a, 102b connected to the harness assembly 54. As best illustrated in FIGS. 2A, 2B and 3, one of the defibrillator electrodes 102a is approximately positioned above the patient's heart at the left side of his or her chest. Another electrode 102b may be placed on the right side of the chest, as shown in FIGS. 2A and 2B. To improve accuracy of the electrical current passing through the patient 24 during operation, the other electrode 102b may be positioned at or on the patient support surface 38, as shown in FIG. 3. The conductive path between the defibrillator electrodes 102a, 102b preferably passes through the patient's heart. Further, the defibrillator electrodes 102a, 102b may comprise needles 104 configured to penetrate through clothing and an outer skin layer of the patient to deliver energy below the outer skin layer of the patient 24. This needle-based configuration may require lower electrical power than traditional AED systems, as the energy is delivered below the statum cornea. This provides advantages of both creating a conductive path through the heart of the patient as well as delivering the energy below the outer skin layer.

The AED 100 may be in electronic communication with the controller 84 and/or the sensor system 86. In one exemplary embodiment, the sensors 88 of the sensor system 86 comprise an electrocardiographic sensor that detects cardiac arrhythmias of ventricular fibrillation and/or ventricular tachycardia. Upon detecting such an event, the sensor system 86 transmits a heart event signal to the AED 100, either directly or indirectly via the controller 84. In response to the heart event signal received from the sensor system 86, the AED 100 operates as intended, generating and transmitting electric current between the defibrillator electrodes 102a, 102b to hopefully reestablish an effective heart rhythm for the patient 24.

The controller 84 may advantageously coordinate operation of the chest compression system 80 and the AED 100 to deliver simultaneous treatment modalities to improve the likelihood of resuscitation. For example, during cardiac arrest, the controller 84 may provide one or more cycles of CPR compressions (i.e., a series of iterative adjustments to the tension of the harness assembly 54, as previously disclosed herein), followed by one or more electric shocks via the AED 100. At least one CPR protocol recommends administration of defibrillation following five cycles each of thirty compressions. The coordinated operation of the compression system 80 and the AED 100 may be repeated or adjusted in any suitable manner based on the real-time physiologic data being gathered by the sensor system 86 during operation of the patient support system 20.

Literature has suggested that elevating the patient's head to allow gravity to help improve blood flow in and out of the brain provides advantages during CPR. The concept, known as "heads-up CPR," is based on the notion that CPR performed while the patient is flat and supine disadvantageously reduces the possibility of a cerebral perfusion gradient. As disclosed above, the section actuator system 106 (FIGS. 1 and 5) coupled to the at least one movable section 35a, 35b is configured to control movement (e.g., the articulation) of the fowler section 35a and the seat section 35b relative to one another and/or to the base 26. FIG. 5 shows that the section actuator system 106 is in electronic communication with the controller 84.

The section actuator system 106 comprises at least one actuator 108 coupled to the at least one movable section 35a, 35b, as illustrated in FIGS. 2 and 3. More than one of the movable sections 35a, 35b may be controlled with a single actuator 108, and/or each one of the movable sections 35a, 35b may be coupled to a separate actuator 108. For example, the patient support apparatus 22 of FIG. 16 may comprise one, two, three or more actuators 108 coupled to the movable section 35a, 35b, 35c. The controller 84 controls the at least one actuator 108 so as to cause movement of one of the fowler section 35a and the seat section 35b relative to one another and/or to the base 26. Often, the fowler section 35a articulates in the direction of arrow 110 (FIG. 3) such that the patient 24 is positioned in an inclined position. The inclined position generally is defined as the upper body of the patient 24 being situated above horizontal at an angle relative to his or her lower body. As applied to the exemplary embodiment illustrated in FIG. 3, the inclined position generally is defined as the fowler section 35a being positioned above horizontal at an angle relative to the seat section 35b. The inclined position may be at an angle of 1, 10, 45, 60, or 90 degrees, or any other suitable angle. The sensors 88 or the sensor system 86 may comprise an angle sensor, gravity sensor, accelerometer, gyroscope, and/or combinations thereof, or any other suitable sensor for measuring the current inclined position (e.g., angle) to enable the controller 84 to operate the actuators 108 to place the fowler section 35a at a desired inclined position.

After moving the at least one movable section 35a, 35b to the desired inclined position, the controller 84 is configured to operate the chest compression system 80 so that the chest compression system 80 provides chest compressions to the patient 24 while the patient 24 is inclined. In any exemplary embodiment, the controller 84 is configured to move the at least one movable section 35a, 35b to a predefined inclination angle so that the chest compression system 80 provides the chest compression to the patient 24 while the patient 24 is at the desired inclined position. The predefined inclination angle may be 1, 10, 45, 60, 90 degrees, or any other suitable angle. In one example, the predefined inclination angle may be between 25 and 35 degrees.

Furthermore, the controller 84 may advantageously coordinate operation of the actuator 108 of the section actuator system 106 and the chest compression system 80 (and the AED 100, if desired). For example, the sensors 88 of the sensor system 86 comprise the electrocardiographic sensor that detects a cardiac arrhythmia. Upon detecting of such an event, the sensor system 86 transmits the heart event signal to the controller 84 (and, if desired, the AED 100, as described above). In response to the heart event signal from the sensor system 86, the controller 84 transmits a control signal to one or more actuators 108 of the section actuator system 106. The fowler section 35a moves (i.e., pivots or otherwise articulates via actuator 108 in FIG. 3) to the desired inclined position at an angle, possibly the predefined inclination angle. During movement of the fowler section 35a, the controller 84 controls the tension adjustment system 68 to maintain the appropriate tension of the harness assembly 54. In such an example, the controller 84 controls the shoulder strap actuators 73a to decrease the tension of the shoulder straps 57a (i.e., release) as the fowler section 35a is articulating to the desired inclined position. Once at the desired inclined position and/or the predefined inclination angle, the controller 84 controls the chest compression system 80. More specifically, the controller 84 controls the tension adjustment system 68 to selectively adjust the tension of the harness assembly 54 in a manner that provides chest compression to the patient 24 while the patient is secured on the patient support surface 38. The sequence of moving the patient to the desired inclined position and providing chest compressions is automated in some embodiments, as time is of the essence during a cardiac event. It is to be understood that the sequence may be repeated or adjusted in any suitable manner based on the real-time physiologic data being gathered by the sensor system 86 during operation of the patient support system 20.

Yet another system or device designed to improve patient care while the patient 24 is secured to the patient support surface 38 of the patient support apparatus 22 may comprise a ventilator 112 (see FIGS. 2A and 2B). The patient support system 20 may comprise the ventilator 112 in communication with the controller 84. The ventilator 112 moves breathable air into and out of the lungs to provide breathing for a patient who is physically unable to breathe or breathing insufficiently.

The controller 84 is configured to control operation of the ventilator 112. Furthermore, the controller 84 is configured to coordinate operation of the ventilator 112 and the operation of the chest compression system 80 so that breathing assistance and the chest compressions are provided to the patient 24 in a coordinated manner. At least one CPR protocol recommends administration of two "rescue breaths" following thirty chest compressions. Using the exemplary protocol as an example, the sensor system 86 may detect a cardiac event associated with breathing insufficiency. The sensors 88 of the sensor system 86 may comprise an oxygen sensor, a carbon dioxide sensor, or the like, that detects, for example, the patient's gas exchange (i.e., delivery of oxygen from the lungs to the bloodstream and the elimination of carbon dioxide from the bloodstream to the lungs) or that a quantity of carbon dioxide being expelled by the patient 24 is outside of a reference range or below a reference threshold. Additionally or alternatively, the sensors 88 of the sensor system 86 may comprise a piezoelectric sensor, accelerometer, gyroscope, strain gauge, or the like, that detects the absence of an expected signal change based on a lack of full expansion and contraction of the patient's chest secondary to breathing. The sensor system 86 transmits the cardiac event signal and a pulmonary event signal to the controller 84.

In response to the cardiac event signal and/or the pulmonary event signal received from the sensor system 86, the controller 84 controls the chest compression system 80 via the tension adjustment system 68 to selectively adjust the tension of the harness assembly 54 in a manner that provides chest compression to the patient 24 while the patient is secured on the patient support surface 38. After a predetermined number of compressions (e.g., thirty compressions), and/or in response to physiologic data gathered by the sensor system 86, the controller 84 controls the ventilator 112 to provide the "rescue breaths" to assist the patient 24 with breathing. The sequence of providing chest compressions and assisting the patient 24 with breathing is automated in some embodiments, and may be repeated or adjusted in any suitable manner based on the real-time physiologic data being gathered by the sensor system 86 during operation of the patient support system 20. Further, the coordinated operation of the chest compression system 80 and the ventilator 112 may be further coordinated with the AED 100 and/or the section actuator system 106 as previously disclosed herein.

To facilitate operation of one or more of the numerous functions of the patient support system 20 disclosed herein, the patient support system 20 may further comprise the display 114 and the user interface 116. One exemplary display 114 is shown in FIGS. 3, 7 and 8. The display 114 is in communication with the controller 84. The display 114 may be embodied as a monitor coupled to any suitable structure of the patient support system 20 or coupled to an ambulance, hospital cart, and the like, or as a portable device such as a smartphone, tablet, personal digital assistant (PDA), laptop, and the like. The display 114 is transportable along with the patient 24 or independently portable.

The display 114 is configured to display any displayable feature or information associated with the patient support system 20. Often, the displayable feature comprises physiologic data as gathered by the sensor system 86. In the exemplary embodiment of the display 114 illustrated in FIGS. 3, 7 and 8, the displayable features are electrocardiographic data, heart rate, and temperature. Other physiologic data may comprise pulse oximetry, respiration rate, blood flow rate, and the like. Additional displayable features may comprise any information associated with operation of the patient support system 20 including, but not limited to, incline angle of the at least one movable section 35a, 35b, tension of the harness assembly 54, and settings associated with the chest compression system 80, AED 100 and/or the ventilator 112.

Operations of the patient support system 20 may be effectuated through the user interface 116. The user interface 116 may be external to or integrated with the display 114. For example, FIGS. 3, 7 and 8 show a series of depressable buttons comprising the user interface 116. In other examples, the user interface 116 is a touch-sensitive feature of the display 114 itself. In other embodiments, the user interface 116 may be remote from the display 114 such as a keyboard, smartphone, tablet, personal digital assistant (PDA), and the like, in electronic communication with the display 114. The user interface 116 is in communication with the controller 84.

In certain embodiments, the display 114 and/or the user interface 116 may be coupled to one or more of the frame rails 40, 42, 44, 46. For example, FIG. 2B shows the display 114 (with or without the user interface 116 integrated therewith) coupled to the frame rail 40. The display 114 may be dockable with the frame rail 40 or otherwise removably coupled thereto. In one exemplary embodiment, the display 114 is fixedly mounted to the frame rail 40 and stowable (e.g., foldable) when not in use. Immediately prior to use, the display 114 may be unstowed, such as by unfolding, to expose the screen.

Referring to FIGS. 6 and 7A-7B, the display 114 and/or the user interface 116 may be disposed on the junction 62. FIG. 6 shows the display 114 disposed on one of the portions 63 of the junction 62, and the user interface 116 disposed on the other one of the portions 63 of the junction 64. FIG. 7A shows the display 114 and the user interface 116 disposed on the main body 75 of the junction 62. The content of the display 114 may be oriented so as to be viewable from adjacent one of the frame rails 40, 42 of the patient support apparatus 22. The user interface 116 may comprise tactile or touch-sensitive buttons as described throughout the present disclosure.

A user may control one or more of the operations of the patient support system 20 through the display 114 and/or user interface 116. For example and with reference to FIGS. 4A and 4B, the display 114 and user interface 116 may be used to move the current position 96 of the patient interface 70. In such an example, the sensors 88 may comprise ultrasonic, fluoroscopic, or x-ray imaging devices that display the bony anatomy of the patient 24 on the display 114. The display 114 may further display the current position 96 of the patient interface 70 (e.g., a schematic representation of the projection 82), the optimal position 90 and/or the predefined tolerance 94 of the optimal position 90 as determined by the sensor system 86 as previously disclosed herein. The optimal position 90 and/or the predefined tolerance 94 of the optimal position 90 may be schematically represented on the display 114 similar to the illustrated embodiment shown in FIG. 4A. Should the user believe that, through the information from the display 114 and/or personal experience, the current position 96 is not within the suitable compression location 92, the user may provide a user input to the user interface 116. The user input may comprise a directional command or other predefined setting to move the current position 96 along axis L and/or axis T (see FIG. 1). In response to the user input, the controller 84 controls the tension adjustment system 68 to move the patient interface 70 within the suitable compression location 92 as previously disclosed herein. Additional exemplary operations of the patient support system 20 that may be controlled through the display 114 and user interface 116 comprise manual operation of the tension adjustment system 68 to provide chest compressions, manual operation of the section actuator system 106 to adjust incline of the at least one movable section 35a, 35b, and manual operation of the AED 100 and/or the ventilator 112. It should be understood that any feature or operation contemplated herein may be controlled through the user interface 116.

An alert device 117 may be provided to provide audible, visual, tactile and/or other alerts to the user in any number of scenarios contemplated herein. As shown in FIG. 5, the alert device 117 is in electronic communication with the controller 84. Exemplary alert devices 117 may comprise speakers, lights, vibratory mechanisms, and the like.

The alert device 117 is configured to provide an alert in response to physiologic functioning of the patient 24 deteriorating outside of normal limits. Most relevantly, the sensors 88 of the sensor system 86 monitor cardiac functioning of the patient 24. Should, for example, the electrocardiographic sensor detect cardiac arrhythmias of ventricular fibrillation and/or ventricular tachycardia and/or cardiac arrest, an alert signal is sent from the sensor system 86 to the alert device 117 via the controller 84. The alert device 117 provides an alert in response to notify attending caregivers of the situation. In another example, the alert device 117 provides an alert when the controller 84 determines that the harness assembly 54 is not properly tensioned and/or properly coupled to the patient support apparatus 22. Among other advantages, ensuring the patient 24 is properly secured provides for patient safety as well as desired operation of the chest compression system 80. Further, the alert device 117 may be configured to provide an alert if the controller 84 determines that the patient interface 70 is not in the suitable compression location 92. Other exemplary functions of the patient support system 20 may be electronically integrated with the alert device 117 as needed.

Throughout the present disclosure, the sensor system 86 is described as a robust electronic system configured to measure, detect, determine or otherwise gather a multitude and variety of data, including but not limited to physiologic, environmental, spatial, and movement data. The data may be stored in memory 118 of the patient support system 20, which may be later accessed by attending caregivers or others. The advantages associated with gathering and storing the data are readily apparent, particularly because of the circumstances typically associated with emergency transport, acute cardiac events, and other medical emergencies.

For example, a patient may be transported to the emergency department while secured to the patient support apparatus 22 of the patient support system 20. Upon arrival at the emergency department, attending caregivers may access electrocardiographic data, heart rate, temperature, pulse oximetry, respiration rate, blood flow rate, among numerous other metrics, from approximately the time when the harness assembly 54 secures the patient 24 on the patient support surface 38. Similarly, attending caregivers may quickly learn whether chest compressions were provided via the chest compression system 80, electric therapy via the AED 100, breathing assistance via the ventilator 112, and the like.

The data from the memory 118 for the same patient requiring use of the patient support system 20 on multiple occasions may be aggregated. Such data advantageously can delineate patient improvement or deterioration over a period of days, weeks, months, or years. The patient-specific data may be transmitted to a patient electronic medical record (EMR) or electronic health record (EHR). Centralizing the data may improve the patient's care across multiple medical providers. The present disclosure envisions that the data from the memory 118 for different patients may be aggregated to generate best practices in certain situations to facilitate improved patient care in the future. The data may reveal trends in symptomatology and corresponding treatment alternatives not otherwise observable through typical reporting methods.

In one example where the patient 24 is transported in an ambulance or other vehicle, the sensor system 86 comprises sensors that may indirectly track vehicle dynamics of the vehicle, as previously disclosed herein. The tracked vehicle dynamics may comprise acceleration, deceleration, g-force during turns, accidents, and the like. The tracked vehicle dynamics may be stored as data in the memory 118, effectively rendering, in many respects, the patient support system 20 a "black box" of the transport vehicle. In particular, data related to an automobile accident, or crash data, may be invaluable for any number of reasons and in any number of situations.

Figure 11:
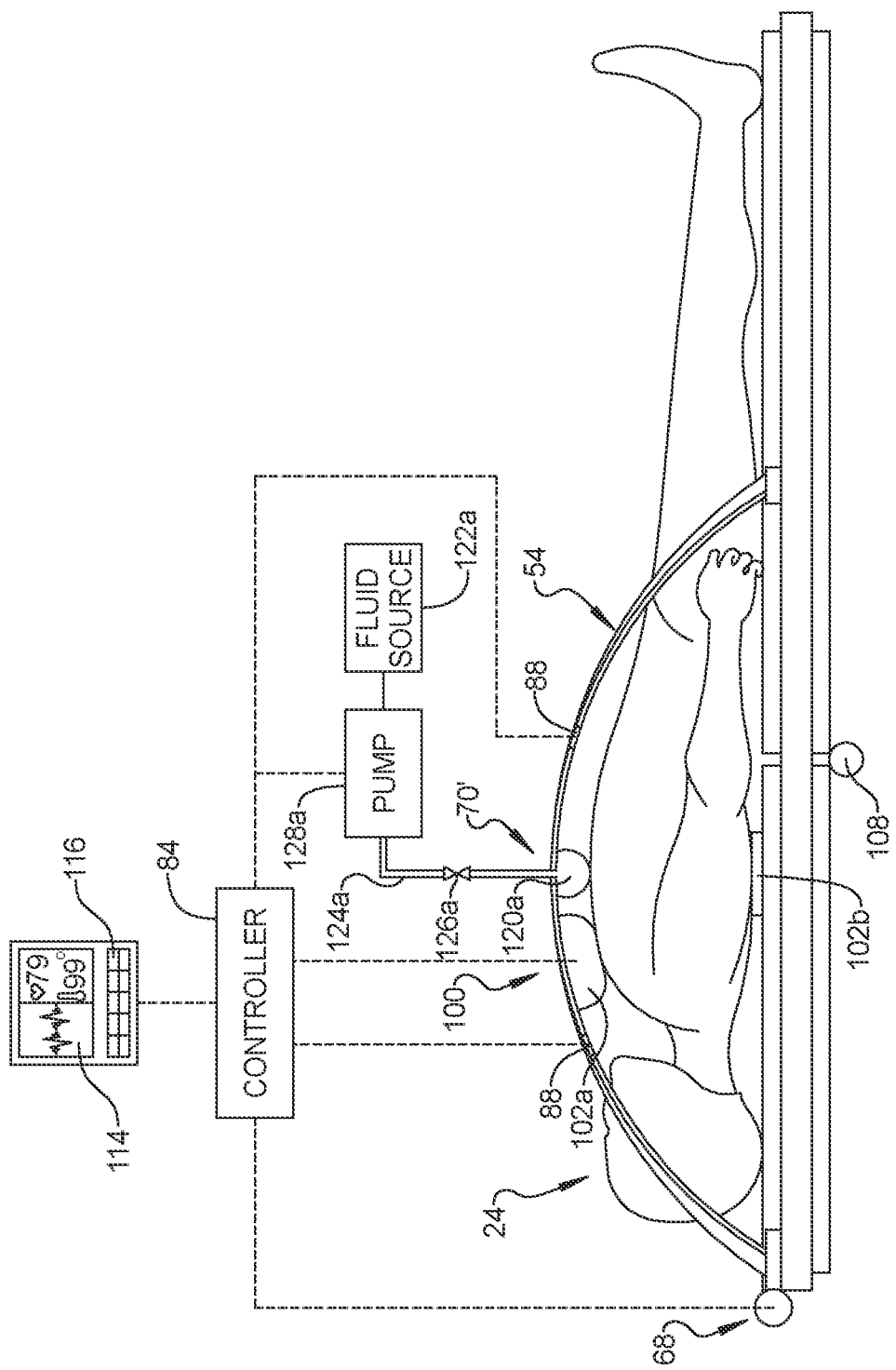
FIG. 11 is an elevational view of the patient support system in accordance with another exemplary embodiment of the present disclosure, the patient support system comprising a harness assembly and a chest compression system.

As mentioned, the patient interface 70 of the chest compression system 80 comprises one or more systems or devices configured to effectuate depressing the chest of the patient 24. In a general sense, the patient interface 70 comprises the structure that is placed in direct contact with the patient 24 during operation of the chest compression system 80. The exemplary embodiment of FIGS. 2A, 2B, 3, 4A and 4B showed the patient interface 70 comprising the projection 82 configured to depress the chest of the patient 24 as the tension of the harness assembly 56 is adjusted. Referring now to FIG. 11, a patient interface 70' in accordance additional exemplary embodiments is shown.

The patient interface 70' comprises one or more bladders 120a, 120b coupled to the harness assembly 54. The bladders 120a, 120b may be integrated into the harness assembly 54 or other suitable structure of the patient support apparatus 22. At least one of the bladders 120a is positioned above the patient's lower sternum, within the suitable compression location 92 (i.e., the predetermined threshold 94 of the optimal compression location 90). Often, the positioning correlates to the junction 62 of the harness assembly 54 similar to the embodiment previously disclosed herein.

The bladders 120a, 120b are configured to be inflated from a deflated state to an inflated state, and conversely deflated to the deflated state from the inflated state. The bladders 120a, 120b are of suitable construction to tolerate the pressures and other operational demands required. One or more fluid sources 122a, 122b are operably connected to the bladders 120a, 120b via fluid lines 124a, 124b. The fluid may comprise a gas such as air, a liquid such as water, or any combination thereof.

The bladders 120a, 120b are configured to be selectively inflated and deflated. To that end, one or more valves 126a, 126b and one or more pumps 128a, 128b are provided. The valves 126a, 126b and/or the pumps 128a, 128b are in communication with the controller 84 as shown in FIG. 5. The controller 84 is configured to control the fluid sources 122a, 122b (via the valves 126a, 126b and the pumps 128a, 128b) to control inflation and deflation of the bladders 120a, 120b. More specifically, controller 84 is configured to control the fluid sources 122a, 122b based on signals from the sensor system 86.

By now well understood in the present disclosure, the chest compression system 80 comprises the tension adjustment mechanism 68 to selectively adjust the tension of the harness assembly 54 in a manner that provides chest compressions to the patient 24 while the patient 24 is secured on the patient support surface 38 with the harness assembly 54. In the present embodiment, providing the chest compressions is further facilitated by selectively inflating and deflating the bladders 120a, 120b. Several non-exhaustive exemplary methods of doing so are contemplated.

In one exemplary method, the bladder 120a is initially in the deflated state. Upon initiation of the chest compression system 80, either via the sensor system 86 or through user input to the user interface 116, the controller 84 operably controls the tension adjustment system 68 to adjust the tension of the harness assembly 54 such that the deflated bladder 120a is drawn into a extremely tight abutting position with the patient 24 in the suitable compression location 92. The controller 84 then operably controls the valve 126a and the pump 128a to selectively supply or transfer fluid from the fluid source 122a via the fluid line 124a to the bladder 120a. The supply of fluid to the bladder 120a inflates the bladder 120a, thereby producing a downward force and depressing the chest of the patient 24. The bladder 120a is selectively deflated to permit the chest to return to its pre-compressed state. It should be appreciated that patent interface 70' is designed to rapidly achieve the high pressures needed to produce the 100 to 125 pounds of force typically required to depress the human chest one and one half to two inches consistent with CPR protocol.

The extent to which the chest of the patient 24 is depressed is monitored with the sensors 88 of the sensor system 86 as previously disclosed herein. Should the chest compressions be too shallow or too deep, the controller 84 is configured to control the tension adjustment system 68 and/or the chest compression system 80 to adjust accordingly.

In another exemplary method, the bladder 120a is initially in the deflated state and positioned in a loose abutting relationship with the patient 24 in the suitable compression location 92. Upon initiation of the chest compression system 80, either via the sensor system 86 or through user input to the user interface 116, the controller 84 operably inflates the bladder 120a, consistent with the previously described exemplary method, beyond a predetermined threshold and possibly to a near-maximum or maximum. In such an inflated state, the bladder 120a is semi-rigid or rigid similar to the projection 82 of the previously described patient interface 70. Then, the controller 84 controls the tension adjustment system 68 to adjust the tension of the harness assembly 54 such that the inflated bladder 120a depresses the chest of the patient 24 in the desired manner. In yet another exemplary method, the controller 84 coordinates the operation of the tension adjustment system 68 and the chest compression system 80 to simultaneously, or by a desired timing offset, adjust the tension of the harness assembly 54 and inflate and deflate the bladders 120a, 120b.

Figure 12A:
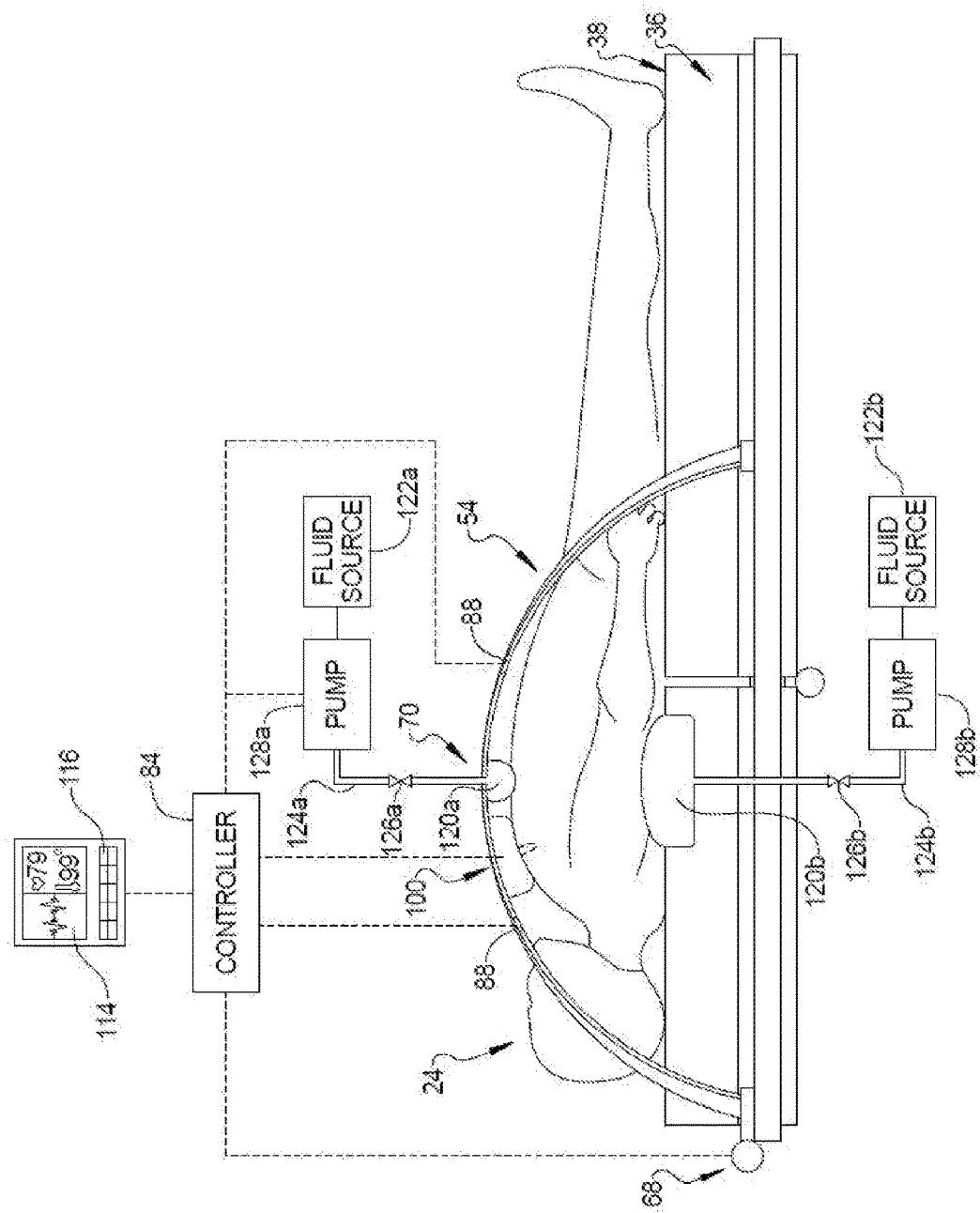
FIG. 12A is an elevational view of the patient support system in accordance with another exemplary embodiment of the present disclosure with the chest compression system including bladders with one of the bladders integrated with the patient support apparatus.

FIG. 12A shows the patient 24 positioned on the mattress 36 of the patient support apparatus 20. The harness assembly 54 secures the patient 24 on the mattress 36. In the present example, the mattress 36 may comprise the patient support surface 38. At least a portion of the chest compression system 80 is integrated into the mattress 36 to provide chest compressions to the patient 24 on the mattress 36. More specifically, the mattress 36 comprises the bladder 120b, introduced above, further comprising the patient interface 70, 70'. As previously described, the bladder 120b is in fluid communication with the fluid source 122b via the fluid line 124b. The valve 126b and the pumps 128a, 128b are in communication with the controller 84, as shown in FIG. 5, which control the selective inflation and deflation of the bladder 120b based on signals received from the sensor system 86.

Whereas the bladder 120a is positioned within the suitable compression location 92 above the patient's lower sternum, the bladder 120b is integrated with or otherwise associated with the mattress 36. In the exemplary embodiment illustrated in FIG. 12A, the bladder 120b is at least partially recessed within the mattress 36. The bladder 120b may also rest upon, be disposed completely within, or be positioned below the mattress 36 (i.e., between the mattress 36 and the patient support deck 34). The bladder 120b is positioned substantially beneath the bladder 120a when the harness assembly 54 secures the patient 24 to the mattress 36 of the patient support apparatus 22.

In some scenarios when the patient 24 is supported on the mattress 36 and the tension adjustment system 68 adjusts the tension of the harness assembly 54 such that the patient interface 70, 70' depresses the chest of the patient 24, a portion of the force from the patient interface 70, 70' is lost. In other words, the full force from the chest compression system 80 is not transferred to the patient 24. A portion of the force may be absorbed by the mattress 36, which is designed to be compressible for the comfort of the patient 24. Also, the suitable compression area 92 is generally above the thoracic spine, and the thoracic spine may flex due to lordosis of the spine.

Providing the bladder 120b positioned underneath the patient 24 opposite the bladder 120a may increase force transference from the chest compression system 80 to the patient 24. That is, inflation of the bladder 120b prior to or simultaneously with the inflation of the bladder 120a effectively "sandwiches" the patient 24 between the bladders 120a, 120b and prevents energy losses due to compressibility of the mattress 36, spinal lordosis, and the like.

In one exemplary method of operation, each of the bladders 120a, 120b is initially in the deflated state. Upon initiation of the chest compression system 80, either via the sensor system 86 or through user input to the user interface 116, the controller 84 operably controls the valves 126a, 126b and the pumps 128a, 128b to selectively supply or transfer fluid from the fluid sources 122a, 122b via the fluid lines 124a, 124b to the bladders 120a, 120b. The supply of fluid to the bladders 120a, 120b inflates the bladders 120a, 120b, thereby producing a downward force from the bladder 120a and an upward force from the bladder 120b (either directly or indirectly via an intervening portion of the mattress 36). The forces collectively depress the chest of the patient 24. Each of the bladders 120a, 120b may be selectively deflated to permit the chest to return to its pre-compressed state. Furthermore, operation of the tension adjustment system 68 to adjust the tension of the harness assembly 54 may be coordinated with the operation of the bladders 120a, 120b in a manner consistent with any of the aforementioned examples.

Inflation of the bladder 120b is immediately prior to or simultaneous with the inflation of the bladder 120a. However, the bladder 120b may be independently inflated and deflated for any number of reasons, including providing chest compressions, chest elevation, promoting comfort of the patient 24, among others. Of course in each of the above examples, all features of the patient support system 20 are considered incorporated by reference in the present embodiment of the patient interface 70'. By way of example only, coordinated operation of the section actuator system 106, the AED 100, and/or the ventilator 112 may be further coordinated and harmonized with the operation of the patient interface 70' of the present embodiment.

Figure 12B:
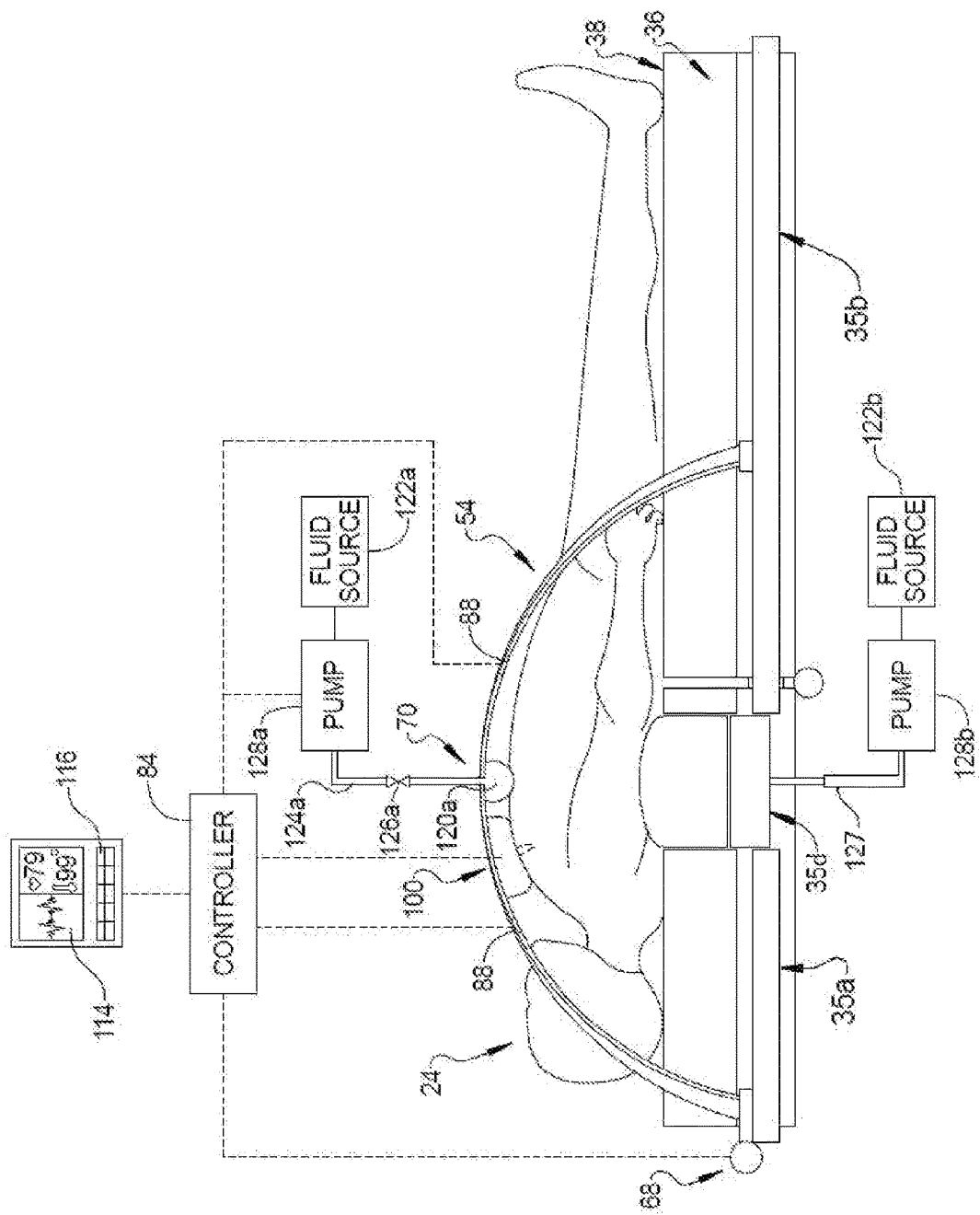
FIG. 12B is an elevational view of the patient support system in accordance with another exemplary embodiment of the present disclosure with the chest compression system including at least one movable section of a patient support deck.

FIG. 12B shows the patient 24 positioned on the mattress 36 of the patient support apparatus 20 with the harness assembly 54 securing the patient 24 on the mattress 36 defining the patient support surface 38. Further, the mattress 36 is supported on the movable sections 35a, 35b, 35d of the patient support deck 34. Similar to previously described embodiments, the fowler section 35a and/or the seat section 35b may be movable relative to one another, for example, to provide for the inclined position of the patient support apparatus 20. In the present embodiment, the movable sections 35a, 35b, 35d includes a compressing section 35d that may be considered integrated into the chest compression system 80. FIG. 12B shows the compressing section 35d positioned beneath the back of the patient. In a manner to be described, the compressing section 35d moves upwardly to provide the chest compression to the patient 24 on the mattress 36. It is noted that while FIG. 12B shows the mattress 36 having discrete sections, one of which is positioned above the compressing section 35d, such an arrangement is merely exemplary and the mattress 36 of previous embodiments may be utilized. It is further contemplated that the compressing section 35d may be an entirety of the patient support deck 34 as opposed to a portion thereof.

The compressing section 35d is coupled to an actuator 127, for example, a hydraulic cylinder in communication with the pump 128b and the fluid source 122b. The actuator 127 moves between a retracted configuration in which the compressing section 35d is substantially aligned with the other movable sections 35a, 35b, and an extended configuration in which the compressing section 35d is positioned above the other movable sections 35a, 35b. The pump 128b is in communication with the controller 84 and configured to direct fluid from the fluid source 122b (e.g., hydraulic fluid) with in a manner sufficient to provide for appreciable upward force necessary for the chest compressions.

The compressing section 35d integrated with the patient support deck 34 cooperates with the tension adjustment system 68 to provide the chest compressions to the patient 24. The tension adjustment system 68 adjusts the tension of the harness assembly 54 such that the patient 24 is secured to the patient support surface 38. In one example, the patient interface 70 is the projection 82 previously described and suitably positioned at the location to provide the chest compressions. The controller 84 actuates the actuator 127 to move the actuator 127 from the retracted to the extended configuration, providing a forceful and sudden upward force to the compressing section 35d and the mattress 36 supported thereon. The upward force provided to the mattress 36 is transferred to the patient 24, who is urged upwardly in a corresponding manner. Yet owing to the tension of the harness assembly 54, the patient 24 is prevented from moving and the projection 82 provides the chest compressions as desired. In another example, the bladder 120a is provided and configured to be operated in the manner previously described. That is, inflation of the bladder 120a prior to or simultaneous with the movement of the compressing section 35d effectively "sandwiches" the patient 24 and prevents energy losses due to compressibility of the mattress 36, spinal lordosis, and the like. Furthermore, operation of the tension adjustment system 68 to adjust the tension of the harness assembly 54 may be coordinated with the operation of the compressing section 35d and/or the bladder 120a in a manner consistent with any of the aforementioned examples. Still further, all features of the patient support system 20 are considered incorporated by reference in the present embodiment of the patient interface 70'. By way of example only, coordinated operation of the section actuator system 106, the AED 100, and/or the ventilator 112 may be further coordinated and harmonized with the operation of the patient interface 70, 70' of the present embodiment.

Figure 13:
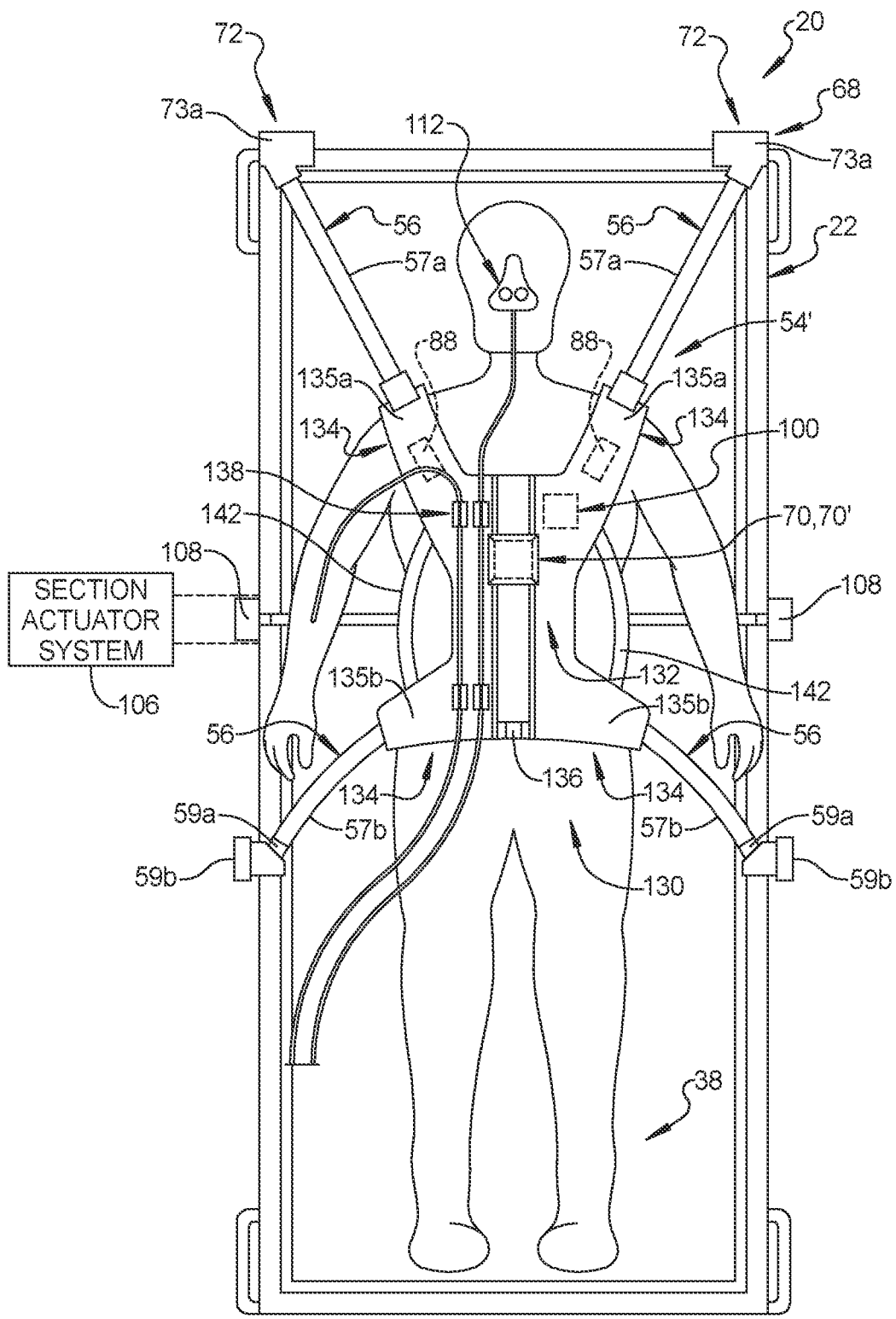
FIG. 13 is a top plan view of a patient support system in accordance with another exemplary embodiment of the present disclosure, the patient support system comprising a harness assembly, a chest pad, and a chest compression system.

Referring now to FIG. 13, a harness assembly 54' in accordance with another exemplary embodiment is illustrated. The harness assembly 54' of FIG. 13 comprises a chest pad 130 configured to secure the bilateral shoulders and bilateral hips of the patient 24 on the patient support surface 38 during transport. FIGS. 9 and 10 show an exemplary embodiment of the chest pad 130. The chest pad 130 comprises a center portion 132 and extension portions 134 generally extending radially from the center portion 132. The extension portions 134 are generally positioned over the bilateral shoulders and the bilateral hips of the patient 24, as illustrated in FIG. 13. More specifically, the extension portions 134 may further comprise shoulder extension portions 135a and hip extension portions 135b configured to secure the shoulders and hips of the patient 24, respectively, to the patient support surface 38. The center portion 132 and extension portions 134 may provide increased comfort for the patient 24 through reduction of areas of increased pressure (i.e., pressure points) often associated with straps. To that end, the chest pad 130 and extension portions 134 may be comprised of any suitable material with mechanical properties to meet the operational demands of the patient support system 20, and preferably provide comfort to the patient 24. One exemplary material comprises neoprene disposed in areas of contact along with cushioning gel as appropriate.

Straps 56 may remain a portion of the harness assembly 54, as illustrated in FIGS. 9 and 10. Each of the shoulder straps 57a may be coupled to one of the shoulder extension portions 135a, and each of the hip straps 57b may be coupled to one of the hip extension portions 135b. The straps 56 and the extension portions 134 may be coupled through any suitable means. For example, FIG. 13 shows the shoulder straps 57a looped through a slot on the shoulder extension portions 135a. The shoulder straps 57a may be fixedly secured to itself (e.g., sewn or otherwise fastened) or to another suitable structure of the harness assembly 54. For another example, FIG. 13 shows the hip straps 57b secured directly to or integral with the hip extension portions 135b. For patient comfort, the length of the extension portions 134 may extend away from the center portion 132 beyond the patient 24 to prevent the straps 56 from directly contacting the patient 24 for comfort.

Figure 14:
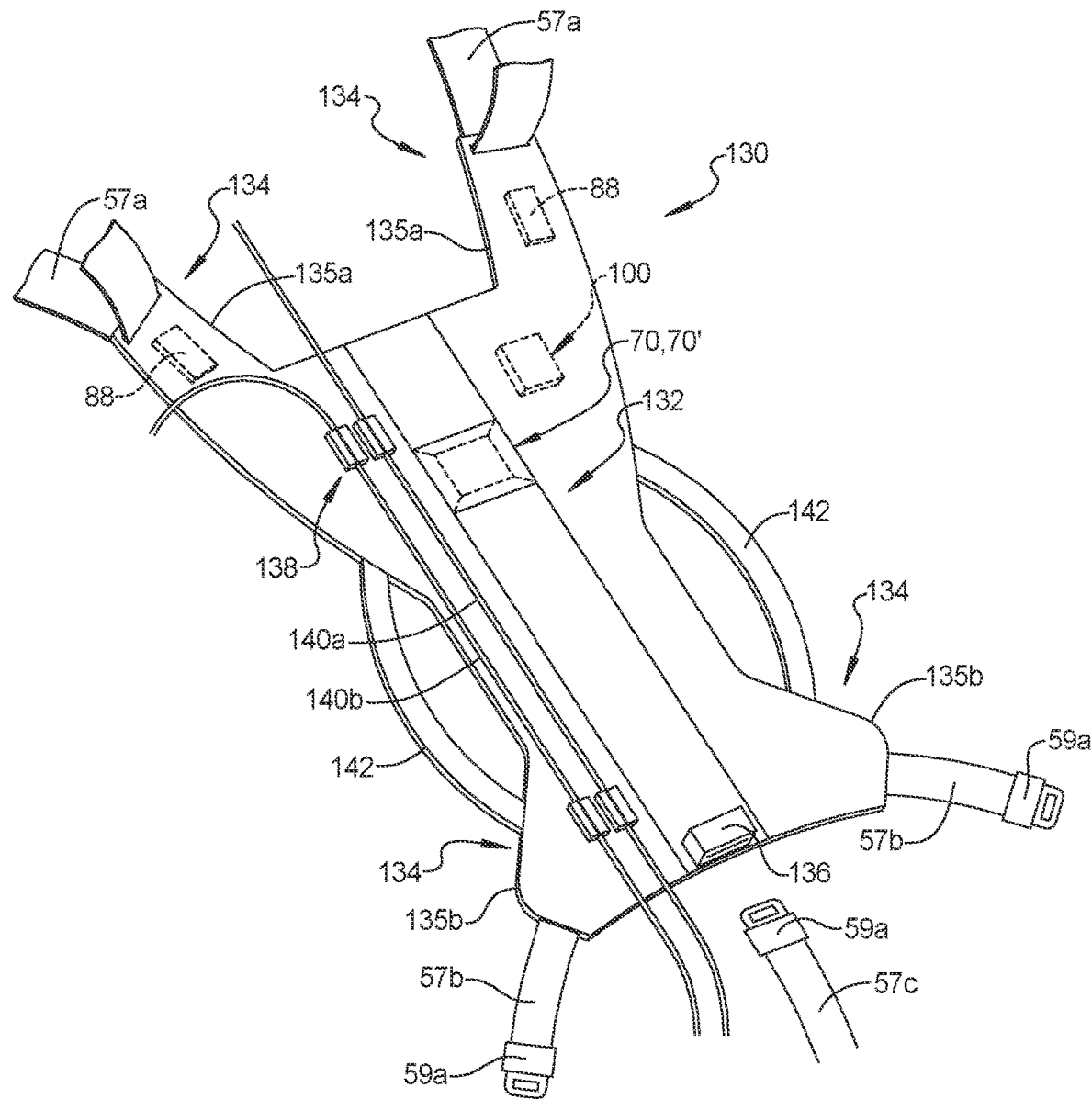
FIG. 14 is a perspective view of the chest pad of FIG. 11.

The chest pad 130 may further comprise a third coupler 136 configured to releasably engage the groin strap 57c, as illustrated in FIG. 14. The third coupler 136 may be coupled to the center portion 132 of the chest pad 130 and generally positioned between the hip extension portions 135b. The exemplary embodiment of FIG. 14 shows the third coupler 136 configured to removably couple to a counterposing first coupler 59a comprising a buckle, but the removable coupling may be effectuated through any suitable means. When coupled, the third coupler 136 and the groin strap 57c may limit or prevent movement of the patient 24 towards the foot end of the patient support surface 38. The incorporation of the groin strap 57c may be particularly advantageous for securing children as well as younger and shorter adults to the patient support surface 38.

Many of the functional components of the patient support system 20 may be advantageously coupled to and/or integrated with the chest pad 130, thereby providing ease of installation or attachment as well as modularity of the patient support system 20 across different operating environments. With continued reference to FIGS. 9 and 10, the patient interface 70, 70', schematically shown in phantom, may be disposed on an underside of the center portion 132 of the chest pad 130 (i.e. between the chest pad 130 and the patient 24). The patient interface 70, 70' is positioned proximate the lower portion of the patient's sternum such that the patient interface 70, 70' is located at the suitable compression location 92 comprising the predefined tolerance 94 from the optimal compression location 90 (FIGS. 4A and 4B).

The patient interface 70, 70' comprising the projection 82 or the bladder 120a may be operably coupled to or integrated with the chest pad 130. For example, the projection 82 may comprise interlocking features configured to removably couple with counterposing interlocking features of the chest pad 130. In another example, the projection 82 is disposed internally within (e.g., "sandwiched" between exterior layers) or otherwise unitary in construction with the chest pad 130. The bladder 120a may be integrated within the chest pad 130 in a similar suitable manner. The interface of the patient interface 70, 70' and the chest pad 130 may take on any known or conventional design, and is not limited to that specifically set forth above.

Further, the sensors 88 of the sensor system 86 may be operably coupled to or integrated with the chest pad 130. FIG. 14 shows one of the sensors 88 positioned on each of the shoulder extension portions 135a. The number and positioning of the sensors on the chest pad 130 may be varied in any suitable manner. Still further, the AED 100 may be operably coupled to or integrated with the chest pad 130, as shown schematically in phantom in FIG. 14. Consistent with earlier embodiments, the AED 100 is positioned over the patient's heart at the left side of the chest.

The harness assembly 54 may further comprise a line management device 138 connected to the chest pad 130. The line management device 138 is configured to organize one or more medical lines 140a, 140b. The exemplary line management device 138 shown in FIGS. 9 and 10 comprises a plurality of clips configured to removably engage the medical lines 140a, 140b. Two sets of clips are illustrated with one positioned at an upper area of the center portion 132 and another position at a lower area of the center portion 132. It is noted that hoops, loops, hooks, hook-and-eye, or any other suitable fastener may be used in addition or as an alternative to the clips.

The configuration of the line management device 138 shown in FIGS. 9 and 10 may orient the medical lines 140a, 140b in an organized manner along the length of the chest pad 130 so as to avoid line entanglement and otherwise impede medical treatment from attending caregivers. More specifically, one of the medical lines 140a may be an oxygen line operably coupled to a nasal cannula comprising components of the ventilator 112 previously disclosed herein. Another one of the medical lines 140b may comprise an intravenous (IV) therapy line coupled to the patient 24 and an IV bag (not shown). The IV line delivers therapy such as medication, saline, and the like, from the IV bag to the patient 24. The exemplary line management device 138 arranges the medical lines 140a, 140b in parallel configuration along the length of the chest pad 130. The line management device 138 may further comprise supplemental structures configured to engage or secure other articles and equipment such as medical devices, medical instruments, personal effects, and the like.

With continued reference to FIGS. 9 and 10, the harness assembly 54' may further comprise handles 142 connected to the chest pad 130. The handles 142 are configured to be grasped by the patient 24 while the patient 24 is secured on the patient support surface 38 with the harness assembly 54'. Exemplary handles 142 illustrated in FIGS. 9 and 10 comprise a pair of elongate, arcuate members each extending from one of the shoulder extension portions 135a to one of the hip extension portions 135b. The handles 142 are positioned to be grasped by the patient 24 with a natural bend at the elbow for patient comfort. Placement and construction of the handles 142 may take on any known or conventional design, and is not limited to that specifically set forth above. For example, the handles 142 may be straight, curved, angled, and the like, and may further comprise discrete grip portions (e.g., neoprene sleeves) overlying or integrated with the handles 142.

The operation of the patient support system 20 wherein the harness assembly 54' comprises the chest pad 130 is substantially the same as the previous embodiments disclosed herein. The sensors 88 may detect a cardiac event such that sensor system 86 provides an event signal to the controller 84. In response to the event signal received from the sensor system 86, the controller 84 controls the actuators 72 of the tension adjustment system 68 to wind the tension elements 74 to adjust the tension of the straps 56. The patient interface 70, 70' depresses the chest of the patient 24 (e.g., using the projection 82, bladders 120a, 120b, etc.). The chest compressions may be repeated or adjusted in any suitable manner based on the real-time physiologic data being gathered by the sensor system 86 during operation of the patient support system 20. The controller 84 may advantageously coordinate operation of the chest compression system 80 and the AED 100, and further coordinate operation of the ventilator 112 to provide breathing assistance and the chest compressions in a coordinated manner. The features of the patient support system 20 described throughout the present disclosure are considered incorporated by reference in the present embodiment of the harness assembly 54'.

Figure 15:
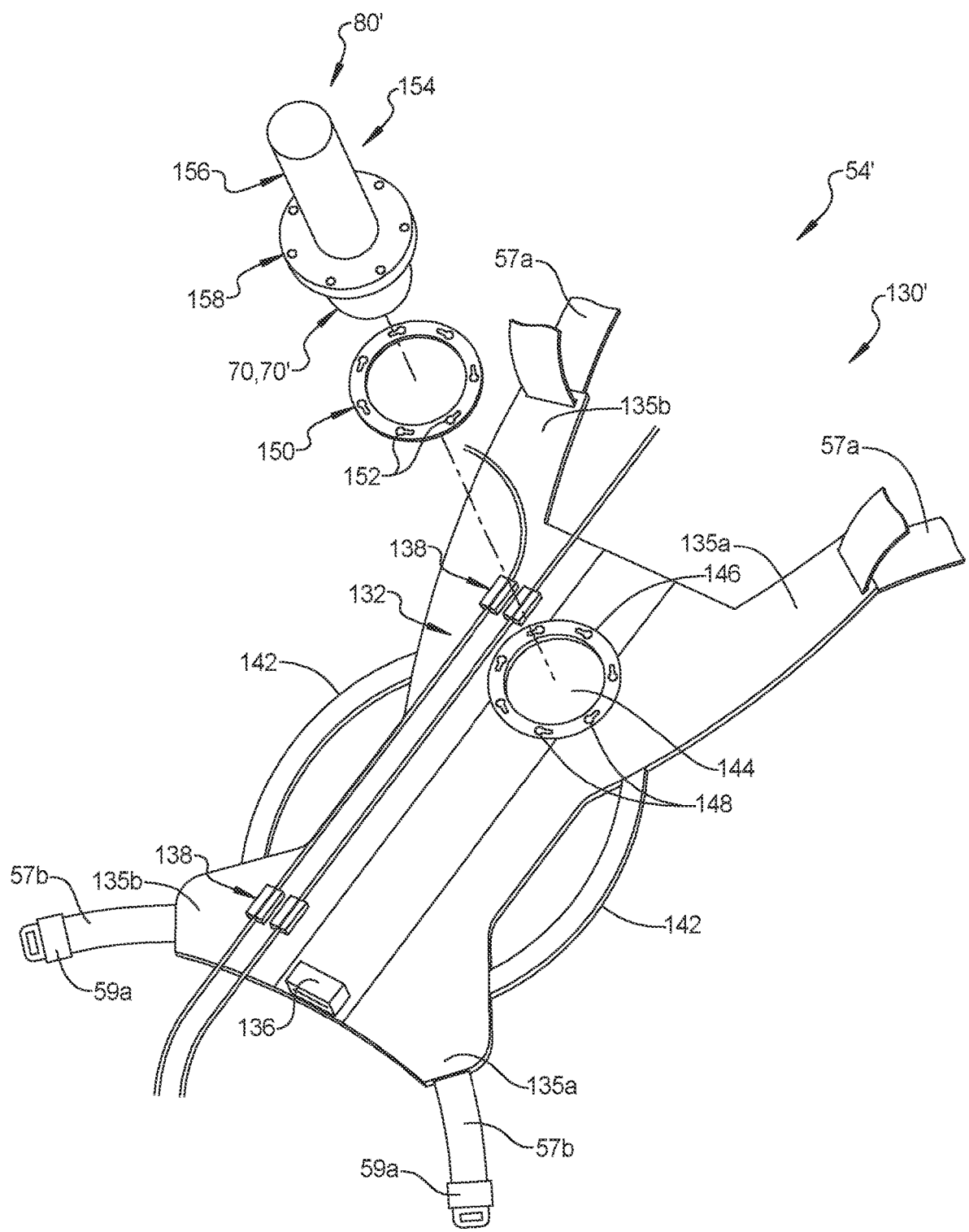
FIG. 15 is an exploded view of another exemplary embodiment of the chest pad and the chest compression system of the patient support system of FIG. 13.

According to another exemplary embodiment illustrated in FIG. 15, the harness assembly 54' comprises a chest pad 130' having an opening 144 positioned adjacent to an adapter 146. The opening 144 extends through the center portion 132 of the chest pad 130', proximate to the suitable compression location 92. In the exemplary embodiment shown in FIG. 15, the opening 144 is generally aligned with a vertical line of symmetry of the chest pad 130'. The adapter 146 is ringed-shaped and encircles the circular opening 144. The adapter 146 comprises one or more interlocking features 148. In the illustrated example, the interlocking features 148 are key-shaped protrusions circumferentially spaced from one another and radially positioned about the ring-shaped adapter 146. The interlocking features 148 may comprise two, three, or four such key-shaped protrusions spaced in any desired manner. Other forms of interlocking features 148 are also contemplated. The adapter 146 may comprise one or more interlocking features positioned proximate the opening 144 in any suitable manner. In most other respects, the chest pad 130' of the present embodiment is the same as the chest pad 130 previously disclosed herein.

With continued reference to FIG. 15, a chest compression system 80' is releasably coupled to the chest pad 130' of the harness assembly 54'. To that end, the chest compression system 80' may comprise a second adapter 150 comprising counterposing interlocking features 152 configured to releasably engage the interlocking features 148 of the adapter 146. In the illustrated exemplary embodiment, the second adapter 150 is ring-shaped and the same or similar in size to the adapter 146 of the harness assembly 54'. The counterposing interlocking features 152 are keyways sized and shaped to removably engage the key-shaped protrusions of the interlocking features 148. The interlocking features 148 and the counterposing interlocking features 152 are releasably engaged by inserting the key-shaped protrusions into the keyways then turning the chest compression system 80' relative to the chest pad 130'. Other forms of counterposing interlocking features 152 are also contemplated.

In an exemplary embodiment, the second adapter 150 is coupled to a head unit 154 of the chest compression system 80' (FIG. 15 shows the second adapter 150 apart from the head unit 154 for clarity). In some cases, the second adapter 150 is fixed to the head unit 154. The head unit 154 of the chest compression system 80' may comprise an actuator portion 156, a flange portion 158, and the patient interface 70, 70'. The second adapter 150 may be secured to the flange portion 158, and the actuator portion 156 may be coupled to the flange portion 158. The actuator portion 156 may coupled to the patient interface 70, 70' to move the patient interface 70, 70' relative to the flange portion 158 to provide chest compressions. Other suitable constructions of the head unit 154 are contemplated.

The chest compression system 80' is configured to be positioned at least partially through the opening 144 of the harness assembly 54' to provide chest compressions to the patient 24 when the chest compression system 80' engages the adapter 146 of the harness assembly 54'. In an exemplary embodiment, the chest compression system 80' comprises an actuator (not shown) within the actuator portion 156 and in communication with the controller 84. In response to a signal from the controller 84, the actuator is configured to move linearly along the major axis of the actuator portion 156 to urge the patient interface 70, 70' into the chest of the patient 24 to perform chest compressions when the harness assembly 54' secures the patient 24 to the patient support surface 38. In such an example, the actuator may be an electromagnetic solenoid comprising an armature slidably disposed within the solenoid. One end of the armature is coupled to the patient interface 70. Other suitable linear actuators are also contemplated. In another example, the head unit 154 may comprise a fluid reservoir, a pump, and a valve (each not shown). The patient interface 70' may be a bladder consistent with earlier exemplary embodiments disclosed herein. In response to a signal from the controller 84, the valve is actuated and the pump urges fluid from the fluid reservoir to pressurize and expand the bladder to perform chest compressions on the patient. In each of the above examples, operation of the tension adjustment system 68 may be coordinated with the operation of the head unit 154 of the chest compression system 80' consistent with the present disclosure described herein. In still another example, the patient interface 70, 70' comprises the projection 82 (with no actuator) that is removably secured through the opening 144 of the harness assembly 54'. The controller 84 controls the tension adjustment system 68 to adjust the tension of the harness assembly 54 such that the projection 82 depresses the chest of the patient 24.

The releasable, detachable or otherwise modular chest compression system 80' of the present embodiment provides several advantages. Until the chest compression system 80' may be needed, the chest pad 130' may operate solely as a harness system without the patient interface 70, 70' positioned against the patient 24. In addition to increasing patient comfort, the chest pad 130' of FIG. 15 achieves a lower profile and removes the obstruction of the head unit 154 extending upwardly from the chest pad 130', thereby permitting attending caregivers to move more freely while treating the patient 24. To that point, the opening 144 of the chest pad 130' provides attending caregivers with access to a portion of the patient's chest for auscultation, injection of medications, manual CPR (if desired), and/or any other maneuvers in the facilitation of patient care. Still further, different iterations or versions of the chest compression system 80' may be selectively coupled to the harness assembly 54' based on the needs of the application or situation. For example, the situation may require the patient interface 70, 70' comprise the projection as opposed to the bladder because, for example, the patient is morbidly obese and more focal pressure is required to achieve the desired chest compression. The modular design of the chest compression system 80' provides for one of several different patient interfaces (e.g., patient interfaces 70, 70') to be quickly swapped during the medical emergency. In some cases, the chest compression system 80' may comprise patient interfaces and associated actuators and controls already known may be attached to the chest pad 130 through the interlocking features 148, 152. One example of an interface and associated actuator and controls may comprise those present on the LUCAS 2 Chest Compression System sold by Physio-Control, Inc. (Redmond, Wash.).

Figure 16:
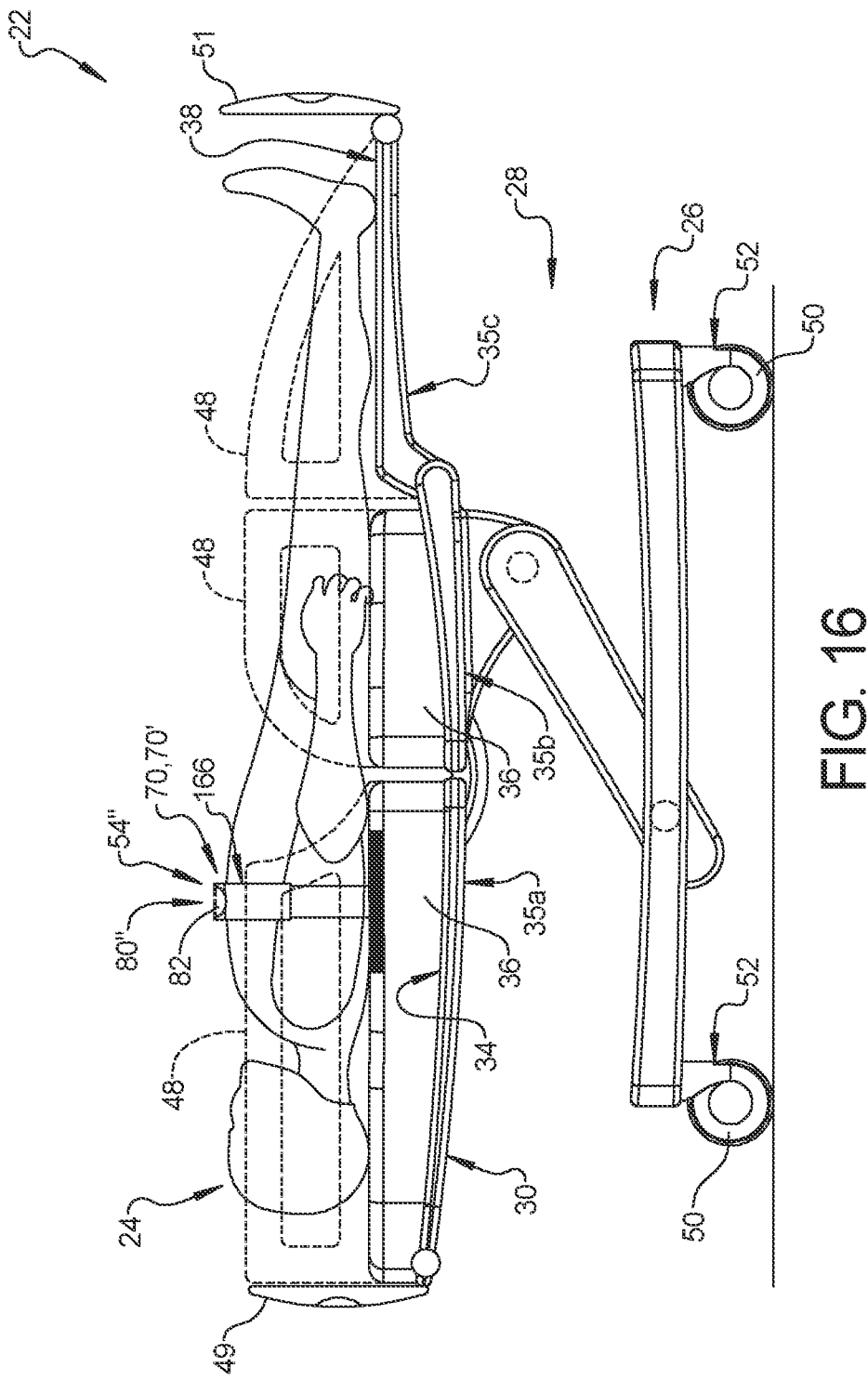
FIG. 16 is a plan view of a patient support system in accordance with another exemplary embodiment of the present disclosure, the patient support system comprising a harness assembly and a chest compression system.

FIG. 16 illustrates the patient support apparatus 22 comprising a hospital bed supporting the patient 24 in the supine position above a floor surface. The patient support apparatus 22 comprises the base 26, the intermediate support assembly 28 disposed above and coupled to the base 26, the support frame 30 coupled to and positioned above the intermediate support assembly 28, and the patient support deck 34 supported by the support frame 30. The at least one movable section 35a, 35b, 35c is operably coupled to the section actuator system 106.

The mattress 36 is disposed on the patient support deck 34. FIG. 16 shows the mattress 36 directly supporting the patient 24. The mattress 36 may be configured to articulate coincident with the movable sections 35a, 35b, 35c of the patient support deck 34. In the exemplary embodiment illustrated in FIG. 16, the mattress 36 comprises the patient support surface 38. The patient support apparatus 22 may comprise side rails or panels 48 at least partially extending above the patient support surface 38 to as to prevent ingress and egress from the patient support apparatus 22. Further, a headboard 49 and/or a footboard 51 may be coupled to the patient support deck 34 or any other suitable structure on the patient support apparatus 22. The headboard 49 and/or the footboard 51 at least partially extend above the patient support deck 34, the mattress 36, and/or the patient support surface 38 to as to prevent ingress and egress from the patient support apparatus 22. Casters 52 comprising wheels 50 are coupled to the base 26 to facilitate transport over the floor surface.

Figure 17:
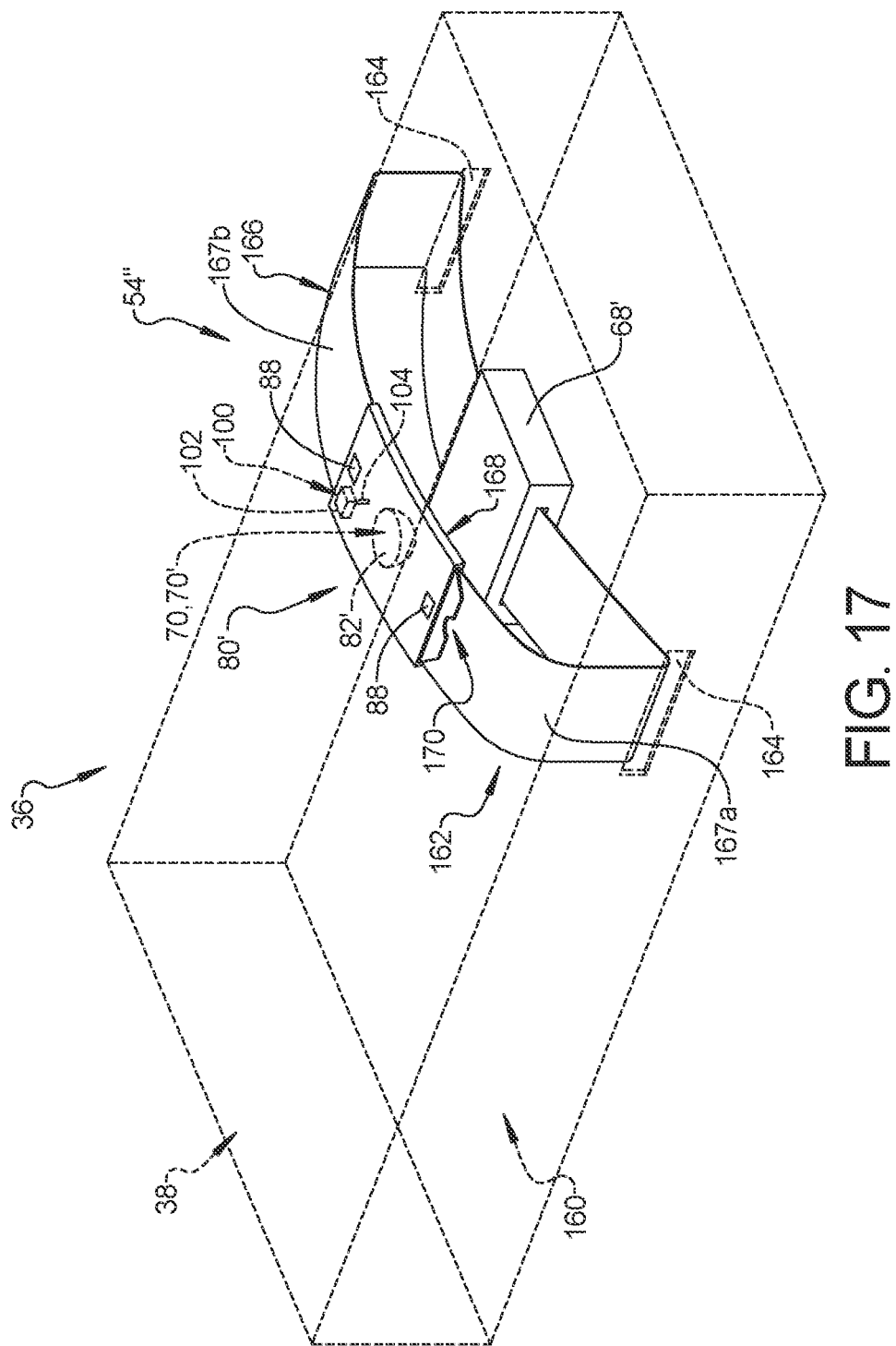
FIG. 17 is a schematic illustration of the chest compression system of FIG. 15.

With concurrent reference to FIG. 17, the harness assembly 54" in accordance with another exemplary embodiment is integrated into the patient support apparatus 22 to provide chest compressions to the patient 24 secured on the patient support deck 34. More specifically, the harness assembly 54" is integrated into the mattress 36. A portion of the mattress 36 of the hospital bed (e.g., a cushion) comprises an exterior surface 160 and an interior 162. The portion of the mattress 36 is schematically represented as a rectangular prism in phantom in FIG. 17. One or more openings 164 extend through the exterior surface 160. The openings 164 may extend inwardly into the interior 162 so as to create one or more channels (not shown) within the interior 162 (through padding and other structures). In the exemplary embodiment illustrated in FIG. 17, the openings 164 comprise slots disposed on opposing sides of the mattress 36. Other positions for the openings 164 are contemplated.

The harness assembly 54" comprises a strap 166 extending traversely across the chest of the patient 24 as illustrated in FIGS. 12 and 13. The strap 166 is positioned so as to extend above the chest of the patient 24 at the suitable compression location 92. The strap 166 may further comprise a first strap portion 167a and a second strap portion 167b. In the illustrated exemplary embodiment, the first strap portion 167a extends from within the interior 162 of the mattress 36, through one of the openings 164, and around and above the right side of the patient 24, and the second strap portion 167b extends from within the interior 162 of the mattress 36, through another one of the openings 164, and around and above the left side of the patient 24. The strap 166 may comprise elongated webbing, but may be constructed in any suitable manner.

The first strap portion 167a and the second strap portion 167b may be releasably coupled via a harness coupler 170. In the embodiment shown, the harness coupler 170 comprises counterposing coupling members, one of which is disposed on the first strap portion 167a and the other of which is disposed on a harness plate 168, which is fixed to the second strap portion 167b. Once the patient 24 is supported by the patient support deck 34 of the patient support apparatus 22, the first strap portion 167a and the second strap portion 167b (along with the harness plate 168) are guided over the chest of the patient 24 and the counterposing coupling members joined, after which the harness assembly 54" secures the patient on the patient support deck 34.

The chest compression system 80" of the present embodiment comprises a tension adjustment system 68'. The tension adjustment system 68' may be disposed within the interior 162 of the mattress 36 as illustrated in FIG. 17. In many functional respects the tension adjustment system 68' of the present embodiment is similar to the tension adjustment system 68 previously disclosed herein. More specifically, the tension adjustment system 68' is operatively coupled to the harness assembly 54" to selectively adjust the tension of the harness assembly 54" in a manner that provides chest compressions to the patient 24 while the patient 24 is secured on the patient support deck 34. In one exemplary embodiment, the tension adjustment system 68' comprises one or more mechanical actuators.

The chest compression system 80" further comprises the patient interface 70, 70'. The patient interface 70, 70' of the chest compression system 80" comprises one or more systems and devices configured to effectuate depressing the chest of the patient 24. The tension adjustment system 68' is configured to adjust the tension of straps 167a, 167b of the harness assembly 54' in a manner that causes the patient interface 70, 70' to forcefully depress the chest of the patient 24. In one example illustrated in FIGS. 12 and 13, the projection 82 is coupled to the harness assembly 54, and more specifically to an underside of the harness plate 168. Further, the sensor system 86 comprises the sensors 88 coupled to the harness plate 168. In the illustrated embodiment, two sensors are disposed on the harness plate 168 and positioned on opposing sides of the patient interface 70, 70'.

The chest compression system 80" and the tension adjustment system 68' are in electronic communication with the controller 84 and the sensor system 86 consistent with previously disclosed embodiments. In operation, the chest compression system 80" is initiated, either via the sensor system 86 or through user input to the user interface 116. For example, sensor system 86 provides an event signal to the controller 84 in response to a cardiac event. The controller 84 operably controls the tension adjustment system 68' to adjust the tension of the harness assembly 54". The one or more mechanical actuators of the tension adjustment system 68' are positioned within the interior 162 of the mattress 36 below the patient support surface 38, and more so below the projection 82. As the tension adjustment system 68' increases the tension of the straps 167a, 167b of the harness assembly 54', the increase in tension has a force component that urges the projection 82 towards the patient 24. The projection 82 depresses the chest of the patient 24 with the desired force to achieve maximum results from the CPR compression. The force with which the projection 82 depresses the chest of the patient 24 may be measured by the sensor system 86. The controller 84 then controls the tension adjustment system 68' to decrease the tension in the straps 167a, 167b to permit the chest to return to its pre-compressed state, thereby completing a single chest compression. The cycle may be repeated, and the tension and compression rate can be adjusted in real-time.

If desired, the AED 100, comprising the electrode 102 and the needle 104, is coupled to the underside of the harness plate 168, may be operated in a coordinated manner with the chest compression system 80". The operation of the AED 100 is disclosed in detail above. Further, all features of the patient support system 20, to the extent compatible with the present embodiment of the harness assembly 54" and the chest compression system 80", are considered incorporated by reference. By way of non-limiting example, the controller 84 may advantageously coordinate operation of the section actuator system 106 and the chest compression system 80". The controller 84 controls the section actuator system 106 to move one of the movable sections 35a, 35b, 35c of the patient support deck 34. Once at the desired inclined position at an angle, possibly the predefined inclination angle, the controller 84 controls the chest compression system 80'. For another non-limiting example, the controller 84 may coordinate operation of the ventilator 112 and the operation of the chest compression system 80" so that breathing assistance and the chest compressions are provided to the patient 24 in a coordinated manner. It is to be understood that these features may adjusted in any suitable manner based on the real-time physiologic data being gathered by the sensor system 86 during operation of the patient support system 20. The features of present embodiment may be incorporated into stretcher, an ambulance cot, or similar apparatus utilized in the transport of a patient.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support system comprising:
   a patient support apparatus comprising a patient support surface;
   a harness assembly including a plurality of straps configured to secure the patient on the patient support surface during transport, wherein at least two of the plurality of straps are coupled to one another at a junction;
   a sensor system integrated into the harness assembly to detect a suitable compression location on the patient;
   a chest compression system operatively attached to the harness assembly, the chest compression system including:
      a patient interface disposed on the junction, and
      a tension adjustment system operatively coupled to the harness assembly, wherein the tension adjustment system comprises one or more actuators coupled to at least one of the plurality of straps; and
   a controller in communication with the chest compression system and with the sensor system, the controller being configured to determine a current position of the patient interface relative to the suitable compression location based on signals received from the sensor system, operate the one or more actuators to move the patient interface to be within a predefined tolerance of the suitable compression location, and control operation of the one or more actuators to increase tension in at least one of the plurality of straps so as to urge the junction towards the patient to provide a chest compression to the patient.

2. The patient support system of claim 1, wherein the patient support apparatus further comprises one or more frame rails with the one or more actuators movably coupled to the one or more frame rails for selectively positioning the harness assembly relative to the patient.

3. The patient support system of claim 1, wherein the tension adjustment system includes one or more pulling elements coupled to at least one of the plurality of straps.

4. The patient support system of claim 3, wherein the controller is further configured to control the one or more actuators to wind the one or more pulling elements and adjust tension of at least one of the plurality of straps.

5. The patient support system of claim 1, wherein the plurality of straps include:
   one or more shoulder straps configured to secure the shoulders of the patient on the patient support surface, and
   one or more hip straps configured to secure the hips of the patient on the patient support surface.

6. The patient support system of claim 1, wherein the harness assembly includes first couplers; and
   wherein the patient support apparatus includes second couplers configured to releasably engage the first couplers.

7. The patient support system of claim 1, further including an automated external defibrillator having defibrillator electrodes connected to the harness assembly.

8. The patient support system of claim 1, wherein the patient support apparatus includes a patient support deck having at least one movable section.

9. The patient support system of claim 8, wherein the controller is configured to move the at least one movable section to an inclined position so that the chest compression system provides chest compressions to the patient while the patient is inclined.

10. The patient support system of claim 9, wherein the patient support apparatus includes an actuator coupled to the at least one movable section.

11. The patient support system of claim 10, wherein the controller is configured to coordinate operation of the actuator and operation of the chest compression system.

12. The patient support system of claim 1, wherein the harness assembly further includes a chest pad configured to secure shoulders and hips of the patient on the patient support surface during transport.

13. The patient support system of claim 12, wherein the chest pad defines an opening; and
   wherein the harness assembly further includes an adapter adjacent to the opening to releasably engage the chest compression system to facilitate providing chest compressions to the patient through the opening with the chest compression system engaging the adapter.

* * * * *